(12) United States Patent
Pastan et al.

(10) Patent No.: US 7,399,827 B1
(45) Date of Patent: Jul. 15, 2008

(54) PAGE-4, AN X-LINKED GAGE-LIKE GENE EXPRESSED IN NORMAL AND NEOPLASTIC PROSTATE, TESTIS AND UTERUS, AND USES THEREFOR

(75) Inventors: Ira Pastan, Potomac, MD (US); Ulrich Brinkmann, Weilheim (DE); George Vasmatzis, Rochester, MN (US); Byungkook Lee, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 499 days.

(21) Appl. No.: 09/763,393

(22) PCT Filed: Aug. 31, 1999

(86) PCT No.: PCT/US99/20046
§ 371 (c)(1),
(2), (4) Date: Jul. 30, 2001

(87) PCT Pub. No.: WO00/12706
PCT Pub. Date: Mar. 9, 2000

Related U.S. Application Data

(60) Provisional application No. 60/098,993, filed on Sep. 1, 1998.

(51) Int. Cl.
C07K 14/00 (2006.01)
(52) U.S. Cl. ............... 530/350; 530/300; 424/185.1; 424/193.1
(58) Field of Classification Search ........... 530/350, 530/300; 424/184.1, 185.1, 277.1, 193.1
See application file for complete search history.

(56) References Cited

U.S. PATENT DOCUMENTS 5,662,907 A  9/1997  Kubo et al.

FOREIGN PATENT DOCUMENTS

WO    WO 94/020127   *  9/1994
WO    WO 98/32855       7/1998

OTHER PUBLICATIONS

Roitt I et al, 1998, Immunology, 4th ed, Mosby, London, p. 7.9.*
Brennan et al (Journal of Autoimmunity, 1989, vol. 2 suppl., pp. 177-186).*
Zimmer (Cell Motility and the Cytoskeleton, 1991, vol. 20, pp. 325-337).*
Eriksson et al (Diabetologia, 1992, vol. 35, pp. 143-147).*
Hell et al (Laboratory Investigation, 1995, vol. 73, pp. 492-496).*
Guo et al (Journal of Pharmacology and Experimental Therapeutics, 2002, vol. 300, pp. 206-212).*
Smith RT, 1994, Clin Immunol, 41(4): 841-849.*
Boon (Adv Can Res, 1992, 58:177-210).*
Ezzell (J. NIH Res, 1995, 7:46-49).*
Spitler (Cancer Biotherapy, 1995, 10:1-3).*
Kirkin et al, 1998, APMIS, 106 : 665-679.*
White et al, 2001, Ann Rev Med, 52: 125-145.*
Bowie et al (Science, 1990, 257 : 1306-1310).*
Bork et al, Genome Research, vol. 10 (2000), pp. 398-400.*
Scott et al, Nature Genetics, vol. 21 (Apr. 1999), pp. 440-443.*
Montesano, R et al,1996, Intl J Cancer, 69(3): 225-235.*
Burmer, GC et al, 1991, Environmental Health perspectives, 93: 27-31.*
Busken, C et al, Digestive Disease Week Abstracts and Itinerary Planner, 2003, abstract No. 850.*
US 20040248256A1 in MPSRCH search report, 2005, us-09-763-393-1.rapb, p. 2, Seq Id No. 2.*
Visseren et al, 1997, Intl J Cancer, 73(1): 125-30.*
Fu et al (EMBO Journal, 1996, vol. 15, pp. 4392-4401).*
Yokota, J et al (Oncogene, 1988, vol. 3, pp. 471-475).*
Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764-767).*
Van Dyke D L et al, 2003, Cancer Genetics and Cytogenetics 241: 137-141.*
Kunkel, P, et al, 2001, Neuro-oncology 3(2): 82-88.*
Brinkmann, U. et al., *PAGE-1, an X chromosome-linked GAGE-like gene that is expressed in normal neoplastic prostate, testis, and uterus*, Proc. Natl. Acad. Sci. USA, vol. 95, pp. 10757-10762, (Sep. 1998).
Buus, S., *Description and prediction of peptide-MHC binding: the 'human MHC project'*, Curr. Opin. Immun., 11: 209-213 (1999).
Celis, E. et al., *Epitope selection and development of peptide based vaccines to treat cancer*, Cancer Biology, vol. 6, pp. 329-336 (1995).
Celis, E. et al., *Induction of anti-tumor cytotoxic lymphocytes in normal humans using primary cultures and synthetic peptide epitopes*, Proc. Natl. Acad. Sci. USA, vol. 91, pp. 2105-2109, (Mar. 1994).
Celis, E. et al., *Identification of Potential CTL Epitopes of Tumor-Associated Antigen Mage-1 for Five Common HLA-A Alleles*, Molecular Immunology, vol. 31, No. 18, pp. 1423-1430, (1994).

(Continued)

*Primary Examiner*—Larry R. Helms
*Assistant Examiner*—Minh-Tam Davis
(74) *Attorney, Agent, or Firm*—Klarquist Sparkman, LLP

(57) ABSTRACT

PAGE-4 is a gene preferentially expressed in normal male and female reproductive tissues, prostate, testis, fallopian tube, uterus and placenta, as well as in prostate cancer, testicular cancer and uterine cancer. This expression pattern makes it a target for diagnosis and for vaccine based therapy of neoplasms of prostate, testis and uterus. The invention provides immunogenic compositions comprising PAGE-4 protein or immunogenic peptides thereof, methods of inhibiting the growth of malignant cells expressing PAGE-4, and methods of inducing an enhanced immune response to PAGE-4-expressing cancers.

11 Claims, 6 Drawing Sheets

OTHER PUBLICATIONS

Chesnut et al., *Design and Testing of Peptide-Based Cytotoxic T-Cell-Mediated Immunotherapeutics to Treat Infectious Diseases and Cancer*, Vaccine Design: The Subunit and Adjuvant Approach, Chapter 38, eds. Powell, M. and Newman, M., Plenum Press, New York (1995).

Gulukota, K. et al., *Two Complementary Methods for Predicting Peptides Binding Major Histocompatibility Complex Molecules*, J. Mol. Biol., 1258-1267 (1997).

Lanzavecchia, A., *Identifying Strategies for Immune Intervention*, Science, vol. 260, pp. 937-944, (May 14, 1999).

Rammensee, H. et al., *MHC ligands and peptide motifs: first listing*, Immunogentics, 41:178-228, (1995).

Schafer, J. et al., *Prediction of well-conserved HIV-1 ligands using a matrix based algorithm, EpiMatrix*, Vaccine, vol. 16, No. 19, pp. 1880-1884 (1998).

Sidney et al., *Broadly Reactive HLA Restricted T Cell Epitopes and Their Implications for Vaccine Design*, Concepts in Vaccine Development, Chapter 2, Ed. Kaufmann, S., Walter de Gryter, Berlin, New York (1996).

Sinigaglia, F. and Hammer, J., *Motifs and Supermotifs for MHC Class II Binding Peptides*, J. Exp. Med., vol. 181, pp. 449-451, (Feb. 1995).

Vasmatzis, G. et al., *Discovery of three genes specifically expressed in human prostate by expressed sequence tag database analysis*, Proc. Natl. Acad. Sci. USA, vol. 95, pp. 300-304 (Jan. 1998).

Vitiello, A. et al., *Comparison of cytotoxic T lymphocyte responses induced by peptide or DNA immunization: implications on immunogenicity and immunodominance*, Eur. J. Immunol., 27:671-678, (1997).

Brinkmann, U. et al., "Novel Genes in the PAGE and GAGE Family of Tumor Antigens Found by Homology Walking in the dbEST Database," *Cancer Research* 59:1445-1448, Apr. 1, 1999.

Brinkmann, U. et al., "PAGE-1, an X chromosome-linked GAGE-like gene that is expressed in normal and neoplastic prostate, testis, and uterus," *Proc. Nat. Acad. Sci. USA* 95:10757-10762, Sep. 1998.

Iavarone, C. et al., "PAGE4 is a Cytoplasmic Protein that is Expressed in Normal Prostate and in Prostate Cancers," *Molecular Cancer Therapeutics* 1:329-335, Mar. 2002.

Ørntoft, T. F. et al, "Genome-wide Study of Gene Copy Numbers, Transcripts, and Protein Levels in Pairs of Non-invasive and Invasive Human Transitional Cell Carcinomas," *Molecular & Cellular Proteomics* 1:37-45, 2002.

Accession No. AA524997, Genbank, Aug. 5, 1997.

Strom et al., *Transcript map in Xp11.23* (unpublished), submitted to EMBL/GenBank/DDBJ databases Apr. 30, 1998, Accession No. AJ005894.

\* cited by examiner

FIG. 1A

```
PAGE    MSARVRSRSRGRGDGQ.EAPDVVAFVAPGE.SQQEEPPT
        || | || ||       ||: :    | : |:: .|| |
GAGE2   MSWRGRSTYRPRPRRYVEPPEMIGPHRPEQPSDEVEPAT
GAGE1            Y         E     M
GAGE3    NLS K  rr         Q     V
GAGE4            rr        Q     M
GAGE5,6          rr        Q     V
        ||   ||  |:| :| ] ] |  :|:|  :    ||: |
MAGE5   MSLEQKSQ-KPEEGLDTQE.EALGLVGVQAATTEEQEAVS
MAGE8       L G   rr A    QA G.  P MD  IP A   K A

PAGE    DNQDIEPGQERE..........GTPPIEERKVEGDCQE
         :: || :|:            | : |.|   ||
GAGE2   P.EEGEPATQRQDPAAAQEGEDEGASAGQGPKPEAHSQE
GAGE1                                       D
GAGE3-6                                     D
            |||  | |||   |       ||    ||
MAGE5   SSSPT.VPGTLGEVPAAGSPGPLK.SPQGASAIPTAIDFTLW
MAGE8        T IM   E  TDS     S PQ.  E    SSL VT S

PAGE    MDLEKTRSERGDGSDVKEKTPPNPKHAKTKEAGDGQP
        =|  |   || |  :|  :|||]    |||-||:  |
GAGE2   QGHPQTGCECEDGPDGQEMDPPNPEEVKTPEEGEKQSQC
GAGE1                    M                MR HYVA..
GAGE3-5                  M
GAGE6                    V
         :  |  |: |:     ||    ||       ||  : |
MAGE5   RQSIKGSSNQEEEGPSTSPDP...ESVFRAALSKKVADLIHFLLLKY
MAGE8    S  DE   SN            AHL  L E DE   E VR   R...
```

FIG. 1B

```
PAGE1   MSA..RVRSRSRGRGDGQEAPDVVAFVAPGES.....
        ||.  |.||.|.:||::||...:|: |...|.
PAGE2   MSELVRARSQSSERGNDQESSQPVGSVIVQEPTEEKR

PAGE3   ..............................MTSF

PAGE1   QEEEPPTDNQGPD...............MEAFQQEL
        |:|||||||||  :                -|' ||!
PAGE2   QQEEPPTDNQDIEPGQEREGTPPIEERKVEGDCQEM
        :  |  :  ||  ||||:      :     |  ||
PAGE3   NKTAPPIESQDYTPGQERDEGALDFQVPSLAAYLWEL

PAGE1   DLEKTRSERGDGSDVKEKTPPNPKHAKTKEAGDGQP
        .|| . |||.:|||| :  .| .|   |||||||
PAGE2   ALLKIEDEPGDGPDVREGIMPTFDLTKVLEAGDAQP
        |:  |||||:|:    :|.|::  |:  ||||:||
PAGE3   TRPKTGGERGDGPNVKGESLPNLEPVKIPEAGEGQPSV
```

Page 4 sequence (bold and underline: open reading frame).

GAAGAATTCGCCAGGCTCTCTGCTGACTCAAGTTCTTCAGTTCACGATCTTCTAGTT
GCAGCG

<u>ATGAGTGCACGAGTGAGATCAAGATCCAGAGGAAGAGGAGATGGTCAGGAGGCTCCC</u>
<u>GATGTGGTTGCATTCGTGGCTCCCGGTGAATCTCAGCAAGAGGAACCACCAACTGAC</u>
<u>AATCAGGATATTGAACCTGGACAAGAGAGAGAAGGAACACCTCCGATCGAAGAACGT</u>
<u>AAAGTAGAAGGTGATTGCCAGGAAATGGATCTGGAAAAGACTCGGAGTGAGCGTGGA</u>
<u>GATGGCTCTGATGTAAAAGAGAAGACTCCACCTAATCCTAAGCATGCTAAGACTAAA</u>
<u>GAAGCAGGAGATGGGCAGCCA</u>

TAAGTTAAAAAGAAGACAAGCTGAAGCTACACACATGGCTGATGTCACATT
GAAAATGTGACTGAAAATTTGAAAATTCTCTCAATAAAGTTTGAGTTTTCTCTGAA

FIG. 5

PAGE-4, AN X-LINKED GAGE-LIKE GENE EXPRESSED IN NORMAL AND NEOPLASTIC PROSTATE, TESTIS AND UTERUS, AND USES THEREFOR

CROSS-REFERENCE TO RELATED APPLICATIONS

This application is a § 371 U.S. national stage of PCT US99/20046 filed Aug. 31, 1999, which was published in English under PCT Article 21(2), which in turn claims the benefit of U.S. Provisional Application 60/098,993 filed Sep. 1, 1998, which is incorporated herein by reference.

STATEMENT REGARDING FEDERALLY FUNDED RESEARCH

Not applicable.

BACKGROUND OF THE INVENTION

ESTs are sequences derived from randomly selected clones from various cDNA libraries (Adams, M. D. et al. *Science* 252:1651-1656 (1991); Adams, M. D. et al. *Nature* 377:3-174 (1995); Adams, M. D. et al., *Nature* 355:632-634 (1992); Emmert-Buck et al., *Science* 274:998-1101 (1996); Krizman, D. B. et al., *Cancer Res.* 56:5380-5383 (1996); Strausberg, R. L. et al., *Nat. Genet.* 16:415-516 (1997)). Each cDNA clone is generated from a transcript, and the frequency and distribution of the many different transcripts in any given tissue depends on the tissue specific activity of the genes. The translation of transcript frequency and distribution into frequency and distribution of EST sequences depends not only on the specificity and magnitude of mRNA expression, but also on other factors such as mRNA stability and clonability of these EST sequences. Therefore, a specificity or frequency analysis of ESTs only provides a guide for the prediction of expression patterns. Nevertheless, ESTs provide a valuable source of information that may be utilized to predict the expression patterns of specific genes in different tissues.

The recently developed NCI Cancer Genome Anatomy Project (CGAP) uses microdissection and laser-capture techniques to generate defined and tissue/tumor specific EST libraries (http://www.ncbi.nlm.nih.gov/ncicgap (Emmert-Buck et al., *Science* 274:998-1101 (1996); Krizman, D. B. et al., *Cancer Res.* 56:5380-5383 (1996); Strausberg, R. L. et al., *Nat. Genet.* 16:415-516 (1997)). CGAP has already accumulated a vast number of tissue-specific sequences and the CGAP sequence data base is rapidly growing with the continuous addition of sequences from different tissues and tumor types. There are many ways by which the EST sequence data can be processed to cluster, sort and filter the cDNA sequences, in order to identify genes that are specifically expressed in certain tissues. Database "mining" for cDNAs that are preferentially or exclusively expressed in defined tissues, or in malignant/neoplastic tissues provides lists of potential target genes for cancer therapy (Emmert-Buck et al., *Science* 274:998-1101 (1996); Krizman, D. B. et al., *Cancer Res.* 56:5380-5383 (1996); Strausberg, R. L. et al., *Nat. Genet.* 16:415-516 (1997); Vasmatzis, G. et al., *Proc. Natl. Acad. Sci., USA* 95:300-304 (1998)). Although in many cases these "candidate genes", which appear tissue specific in database analyses, cannot be confirmed in their specificity by experimental techniques (e.g. Northern blots or PCR), a reasonable number of candidate genes remain for which the predicted and desired expression pattern can be experimentally confirmed (Vasmatzis, G. et al., *Proc. Natl. Acad. Sci., USA* 95:300-304 (1998); He, W. W. et al., *Genomics* 43:69-77 (1997)). These specifically expressed genes are of interest because of their functions in cell or tumor biology and may also be directly used as markers for cancer diagnosis and as the basis for a variety of methods of therapy.

One method of therapy is to use the gene product as a vaccine to enhance the patient's immune response to the cancer. T cells play an important role in tumor regression in most murine tumor models. Tumor infiltrating lymphocytes ("TIL") that recognize unique cancer antigens can be isolated from many murine tumors. The adoptive transfer of these TIL plus interleukin-2 can mediate the regression of established lung and liver metastases (Rosenberg, S., et al., Science 233: 1318-1321 (1986). In addition, the secretion of IFN-.gamma. by injected TIL significantly correlates with in vivo regression of murine tumors suggesting activation of T-cells by the tumor antigens. (Barth, R., et al., J. Exp. Med. 173:647-658 (1991)). In humans, the ability of tumor TIL to mediate the regression of metastatic cancer in 35 to 40% of melanoma patients when adoptively transferred into patients with metastatic melanoma attests to the clinical importance of the antigens recognized (Rosenberg, S., et al., N Engl J Med 319: 1676-1680 (1988); Rosenberg S., J. Clin. Oncol. 10:180-199 (1992)).

T cell receptors on CD8+ T cells recognize a complex consisting of an antigenic peptide (9-10 amino acids for Human Leukocyte Antigen ("HLA")-A2), β-2 microglobulin, and class I major histocompatibility complex ("MHC") heavy chain (HLA-A, B, C, in humans). Peptides generated by digestion of endogenously synthesized proteins are transported into the endoplasmic reticulum, bound to class I MHC heavy chain and β-2 microglobulin, and finally expressed in the cell surface in the groove of the class I MHC molecule. Therefore, T cells can detect molecules that originate from proteins inside cells, in contrast to antibodies that detect molecules expressed on the cell surface. Antigens recognized by T cells thus may be particularly useful for inhibiting the progression of cancer.

Strong evidence that an immune response to cancer exists in humans have been provided by, for example, the existence of lymphocytes within melanoma deposits. These lymphocytes, when isolated, are capable of recognizing specific tumor antigens on autologous and allogeneic melanomas in an MHC restricted fashion. (Kawakami, Y., et al., J. Immunol. 148:638-643 (1992); Hom, S., et al., J. Immunother. 13:18-30 (1993)). TIL from patients with metastatic melanoma recognize shared antigens including melanocyte-melanoma lineage specific tissue antigens in vitro (Kawakami, Y., et al., J. Immunother. 14:88-93 (1993); Anichini, A. et al., J. Exp. Med. 177:989-998 (1993)).

Although several tumor associated antigens ("TAA") have been found for melanoma, there is a need to identify tissue specific genes whose expression is associated with cancers of other tissues.

SUMMARY OF THE INVENTION

This invention provides a new class of proteins which are preferentially expressed by cells of reproductive tissues, including, but not limited to, the prostate gland, testis, uterus, fallopian tubes, and placenta. The proteins are found in both normal and cancerous reproductive tissues. These proteins share some homology with the GAGE and MAGE family of proteins.

In particular, the invention provides the PAGE-4 protein. The PAGE-4 protein and immunogenic peptides thereof can be used as immunogenic compositions to raise cytotoxic T lymphocyte responses against cells expressing PAGE-4 in vitro or in vivo. Such cells include cancers of the prostate, testis, and uterus. Nucleic acids encoding the protein or an immunogenic peptide thereof can also as immunogenic compositions.

In addition to the uses as immunogenic compositions, the present invention also provides for methods of detecting the presence of the PAGE-4 protein in cells in cell samples or body tissues. The detection can be performed by detecting the protein, typically by using antibodies. Detection of the presence of the protein can also be accomplished by detecting nucleic acids that encode the proteins. Conveniently, this can be done by using detectable probes complementary to all or a portion of sequences encoding PAGE-4. The presence of PAGE-4 in tissues not related to reproduction could be indicative of the spread of cancerous reproductive tissue.

In addition to diagnostic and vaccine uses, PAGE-4 protein and the nucleic acids encoding it can be used in therapeutic applications. PAGE-4 protein can be used to raise antibodies which can be used not only in the diagnostic assays described above, but also as the targeting moiety of immunoconjugates. The toxic moiety of the immunoconjugates can include, but is not limited to, toxins such as ricin, abrin, diphtheria toxin and subunits thereof, as well as botulinum toxins A through F, and *Pseudomonas* exotoxin (PE).

DESCRIPTION OF THE DRAWINGS

FIGS. 1A-B: Similarity of PAGE-4, GAGE and MAGE: (A) The predicted PAGE-4 reading frame is derived from the full length PAGE-4 EST clone nh32c06. The GAGE and MAGE sequences are from SW: GGE1, GGE2, GGE3, GGE4, GGE5, GGE6, MAG5 and MAG8_HUMAN. Note that the "MAGE-alignment" matches amino acids that occur in MAGE5 and/or MAGE8, which are similar to PAGE-4 and/or GAGE1-6; the homologies between single members of the MAGE and PAGE and GAGE protein families are weaker. (B) Alignment of PAGE-1 with other PAGEs. PAGE-2 was translated from the EST ai61a04 EST-cluster and PAGE-3 from om29f08. PAGE-3 was translated from one single EST and it is possible that the truncated amino terminus results from a sequence artifact (the homology extends further to the N-terminus in another reading frame). Several other so far undefined EST clusters were found that have homology to PAGE as well as to GAGE. These clusters do not have the striking similarities that the other GAGE family members have to each other, but they are also not significantly more similar to PAGE than to GAGE. Representatives of some of these cDNA clusters are the ESTS yd88e11 (fetal liver/spleen), yw86a06 (placenta) and yi21h01 (placenta).

FIG. 5: Nucleotide sequence encoding PAGE-4 (SEQ ID NO: 13): The open reading frame is in bold type and underlined.

DETAILED DESCRIPTION

I. Introduction

Figure 2A:
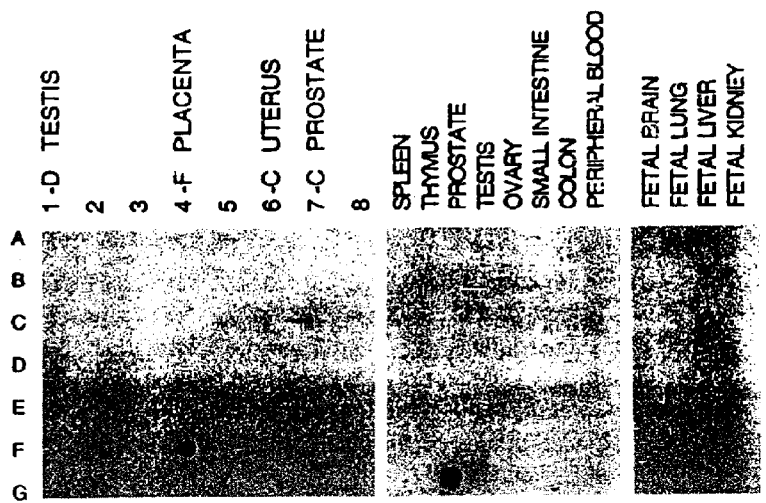
FIGS. 2A-C: Hybridization analysis of PAGE-4 expression: (A) A MTN Dot blot (left) and Northern blots (middle to right) were probed with a 140 bp 32P labeled PAGE-4 probe under very stringent hybridization conditions (50% formamide, 55° C.). Specific PAGE-4 signals were observed in prostate, testis, placenta and uterus, but not in other tissues (Table 1 legend lists the analyzed tissues). Because the hybridization probe had some similarity with another PAGE-4-like EST cluster that is expressed in testis (PAGE represented by the EST zv62h08, Table 2), we additionally used a probe with minimal homology to zv62h08 to confirm that the signal in testis corresponds to the expression of the authentic PAGE-4. (B) Blots containing 20 µg/lane total RNA from normal or malignant ovary (right), fallopian tube (middle) and uterus (left) were hybridized under stringent conditions. PAGE-4 is expressed in fallopian tube, uterus and uterine cancer, but not in ovary and ovarian cancer.

Here we describe the identification of an X-linked gene that is expressed in normal and malignant male and female reproductive tissues. This gene, PAGE-4 (which we originally called PAGE-1 and have now renumbered to be consistent with other findings), is homologous to a family of MAGE/GAGE like proteins and is expressed in normal prostate, testis, uterus, fallopian tube and placenta, as well as in prostate, testicular and uterine cancers.

Prostate, testicular, and uterine cancers, are usually treated, in part, by the surgical removal of the affected organ. The metastases may not, however, be susceptible to surgical removal, or they may be too small to be readily detected. Enhancing the patient's immune response to the cancer, and particularly enhancing the response of cytotoxic T lymphocytes ("CTLs") to the cancer, can aid in slowing or stopping the progress of the disease. PAGE-4 and immunogenic peptides thereof can be used as a vaccine to enhance a patient's immune response against PAGE-4-expressing cancers. Vaccines of DNA encoding the protein or an immunogenic portion thereof can also be used. The vaccines can be administered with adjuvants which help induce a CTL response to the antigen. Since healthy people have tissues which express PAGE-4, it is contemplated that the vaccines of the invention would be used as therapeutic vaccines, rather than as prophylactic vaccines. The identification of this new gene therefore arms researchers and clinicians with a new weapon with which to attack prostate cancer, testicular cancer, and other disorders in which death of the specific tissues might be beneficial to the patient.

Because the PAGE-4 gene is expressed in reproductive tissues, the gene product can be used as a target for reagents directed to cells of these organs. Reagents specific for the gene or the gene product can be used in in vitro assays. For example, the presence of PAGE-4-expressing tissue in a biopsy from a non-reproductive organ may be indicative of the presence of a metastasis from a prostate or uterine cancer. Reagents with appropriate labels can also be used in in vivo assays for the same purpose. For example, radiolabeled antibodies directed against PAGE-4, or against PAGE-4 expressed in conjunction with molecules of the major histocompatibility complex ("MHC"), can be administered to a patient and their presence in various parts of the body then detected to determine whether metastatic cells of a prostate, testicular, ovarian, or other PAGE-4-expressing cancer have invaded other organs or portions of the body.

In addition to these diagnostic uses, the invention permits targeting cells which express PAGE-4 with reagents intended to kill those cells or to modulate their activity. For example, antibodies which specifically recognize PAGE-4, can be used as the targeting moiety of immunotoxins. Since the normal tissues in which the gene is expressed are not essential to the survival of the individual, selective killing of the cells expressing the PAGE-4 gene can eliminate cancerous cells without the severe systemic effects of conventional cancer chemotherapeutic agents.

After defining some of the terms used herein, the discussion below sets forth the discovery of the nature of the PAGE-4 gene and its expression and significance. A discussion of vaccines is provided, as are in vitro and in vivo uses of the invention. The discussion then turns to the making of antibodies against the PAGE-4 protein, the use of those antibodies to form immunoconjugates, such as immunotoxins, and methods of linking effector molecules (such as toxins) to targeting molecules (such as antibodies). The discussion further describes pharmaceutical compositions, such as those containing vaccines, antibodies or immunoconjugates of the invention, as well as diagnostic kits using antibodies or nucleic acids.

II. Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention which can be had by reference to the specification as a whole. Accordingly, the terms defined immediately below are more fully defined by reference to the specification in its entirety.

"PAGE-4" is a gene expressed in prostate and other tissues. In particular, it is expressed in cancers of the prostate, ovaries, and testicles. The sequence of the PAGE-4 gene is set forth in FIG. 5. As used herein, a "PAGE-4 protein" refers to the protein encoded by the PAGE-4 gene. With respect to immunogenic compositions comprising a PAGE-4 protein, it further refers to variations of this protein in which there are conservative substitutions of one or more amino acids of the protein, or deletions or insertions of one or more amino acids, so long as the variations do not alter by more than 20% the ability of the protein, when bound to a Major Histocompatibility Complex class I molecule, to activate cytotoxic T lymphocytes against cells expressing wild-type PAGE-4 protein.

The term "peptide" is used to designate a series of amino acid residues, typically L-amino acids, connected to each other typically by peptide bonds. The peptides of the invention are less than about 30 residues in length, and usually consist of between about 7 and 15 residues, preferably about 8 to 111 residues, and most preferably are 9 or 10 residues.

As used herein, a "PAGE-4 peptide" is a series of contiguous amino acid residues from the PAGE-4 protein between 7 and 20 amino acids in length, preferably about 8 to 11 residues, and most preferably 9 or 11 residues. With respect to immunogenic compositions comprising a PAGE-4 peptide, the term further refers to variations of these peptides in which there are conservative substitutions of one or more amino acids, so long as the variations do not alter by more than 20% the ability of the peptide, when bound to a Major Histocompatibility Complex Class I molecule, to activate cytotoxic T lymphocytes against cells expressing wild-type PAGE-4 protein. Induction of CTLs using synthetic peptides and CTL cytotoxicity assays are taught in, e.g., U.S. Pat. No. 5,662,907.

"Major Histocompatibility Complex" or "MHC" is a generic designation meant to encompass the histocompatibility antigen systems described in different species, including the human leukocyte antigens ("HLA").

An "immunogenic peptide" is a peptide which comprises an allele-specific motif or other sequence such that the peptide will bind an MHC molecule and induce a cytotoxic T lymphocyte ("CTL") response against the antigen from which the immunogenic peptide is derived. Immunogenic peptides are conveniently identified using sequence motifs or other methods, such as neural net or polynomial determinations, known in the art (see discussion, infra). Typically, algorithms are used to determine the "binding threshold" of peptides to select those with scores that give them a high probability of binding at a certain affinity and will be immunogenic. The algorithms are based either on the effects on MHC binding of a particular amino acid at a particular position or the effects on binding of a particular substitution in a motif-containing peptide. Within the context of an immunogenic peptide, a "conserved residue" is one which appears in a significantly higher frequency than would be expected by random distribution at a particular position in a peptide. Typically, a conserved residue is one where the MHC structure may provide a contact point with the immunogenic peptide.

"Negative binding residues" are amino acids which, if present at certain positions (for example, positions 1, 3, or 7 of a 9-mer), will result in a peptide being a nonbinder or poor binder and in turn will fail to be immunogenic (i.e., will fail to induce a CTL response).

The term "motif" refers to the pattern of residues in a peptide of defined length, usually about 8 to about 11 amino acids, which is recognized by a particular MHC allele. The peptide motifs are typically different for each MHC allele and differ in the pattern of the highly conserved residues and negative binding residues.

As used herein, "immunogenic composition" refers to a composition comprising a PAGE-4 protein or a peptide derived from a PAGE-4 protein, which peptide, when bound to a MHC class I molecule, induces a measurable CTL response against cells expressing PAGE-4 protein (a "PAGE-4 peptide"). It further refers to isolated nucleic acids encoding a PAGE-4 protein or a PAGE-4 peptide. For in vitro use, the immunogenic composition may consist of the isolated protein or peptide. For in vivo use, the immunogenic composition will typically comprise pharmaceutically acceptable carriers or other agents. Vaccines are an especially important embodiment of immunogenic compositions for in vivo use. Any particular peptide, PAGE-4 protein, or nucleic acid can be readily tested for its ability to induce a CTL response by art-recognized assays taught further herein.

The term "isolated" refers to material which is substantially or essentially free from components which normally accompany it as found in its native state.

The term "residue" refers to an amino acid or amino acid mimetic incorporated in an oligonucleotide by an amide bond or amide bond mimetic.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv), disulfide stabilized (dsFv) Fv fragments (See, U.S. Ser. No. 08/077,252, incorporated herein by reference), or pFv fragments (See, U.S. Provisional Patent Applications 60/042,350 and 60/048,848, both of which are incorporated herein by reference.) The term "antibody" also includes antigen binding forms of antibodies (e.g. Fab', F(ab')$_2$, Fab, Fv and rIgG. See also, Pierce Catalog and Handbook, 1994-1995 (Pierce Chemical Co., Rockford, Ill.)).

An antibody immunologically reactive with a particular antigen can be generated by recombinant methods such as selection of libraries of recombinant antibodies in phage or similar vectors. See, e.g., Huse, et al., *Science* 246:1275-1281 (1989); Ward, et al., *Nature* 341:544-546 (1989); and Vaughan, et al., *Nature Biotech.* 14:309-314 (1996).

The phrase "single chain Fv" or "scFv" refers to an antibody in which the heavy chain and the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable heavy chain to the variable light chain.

The term "contacting" includes reference to placement in direct physical association.

The terms "conjugating," "joining," "bonding" or "linking" refer to making two polypeptides into one contiguous polypeptide molecule. In the context of the present invention, the terms include reference to joining a ligand, such as an antibody moiety, to an effector molecule (EM). The linkage can be either by chemical or recombinant means. Chemical means refers to a reaction between the antibody moiety and the effector molecule such that there is a covalent bond formed between the two molecules to form one molecule.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (*Proc. Nat'l Acad. Sci. USA* 82:2306-2309 (1985), or the ciliate *Macronucleus*, may be used when the nucleic acid is expressed in using the translational machinery of these organisms.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of an expression vector. Host cells may be prokaryotic cells such as *E. coli*, or eukaryotic cells such as yeast, insect, amphibian, or mammalian cells.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "therapeutic agent" includes any number of compounds currently known or later developed to act as antineoplastics, anti-inflammatories, cytokines, anti-infectives, enzyme activators or inhibitors, allosteric modifiers, antibiotics or other agents administered to induce a desired therapeutic effect in a patient.

The term "immunoconjugate" includes reference to a covalent linkage of an effector molecule to an antibody. The effector molecule can be an immunotoxin.

The term "toxin" includes, but is not limited to, reference to abrin, ricin, *Pseudomonas* exotoxin (PE), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (e.g., domain Ia of PE and the B chain of DT) and replacing it with a different targeting moiety, such as an antibody.

The term "chimeric molecule," as used herein, refers to a targeting moiety, such as a ligand or an antibody, conjugated (coupled) to an effector molecule.

"Targeting moiety" refers to a portion of a chimeric molecule intended to provide the molecule with the ability to bind specifically to the PAGE-4 protein. A "ligand" is a targeting molecule specific for the PAGE-4 protein and is generally synonymous with "targeting moiety." An antibody is one version of a ligand.

The terms "effector molecule," "effector moiety," "EM" "therapeutic agent" and "diagnostic agent," or similar terms, refer to the portion of a chimeric molecule that is intended to have a desired effect on a cell to which the chimeric molecule is targeted. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-PAGE-4 antibody, may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., *Pharm. Ther.* 28:341-365 (1985). Diagnostic agents or moieties include radioisotopes and other detectable labels.

A "conservative substitution," when describing a peptide or protein refers to a change in the amino acid composition of the peptide or protein that does not substantially alter the protein's activity, including its binding to an HLA allele of interest. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The six groups in the following table each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W.H. Freeman and Company (1984).

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "conjugating," "joining," "bonding" or "linking" refer to making two polypeptides into one contiguous polypeptide molecule. In the context of the present invention, the terms include reference to joining an antibody moiety to an effector molecule (EM) and to joining a lipid or other molecule to a protein or peptide to increase its half-life in the body. The linkage can be either by chemical or recombinant means. Chemical means refers to a reaction between the antibody moiety and the effector molecule such that there is a covalent bond formed between the two molecules to form one molecule.

III. Identification of the PAGE-4 Gene

A. Database "Mining"

We identified the gene through a computer screening strategy we established specifically to identify genes that are preferentially expressed in normal prostate and in prostate cancer (Vasmatzis, G. et al., *Proc. Natl. Acad. Sci., USA* 95:300-304 (1998)). Using this approach in combination with experimental verification, we have found several candidate genes that are preferentially expressed in the prostate and are evaluating these genes as targets for the diagnosis or therapy of prostate cancer. PAGE-4 was identified by relaxing the specificity requirements for candidate ESTs in our screening procedure. Instead of removing or giving low ranking to EST clusters which are expressed in non-prostate tissues, we have allowed ESTs that occur in tumors and in a limited number of non-essential normal tissues. Our rationale for this approach is that the expression of a gene in a nonessential tissue and in more than one type of tumor does not exclude it as a target for therapy. In fact, expression in several types of tumors is desirable because this broadens the application of reagents that are developed based upon such targets.

The database analysis was performed on the complete human EST sequence set in the dbEST database (NCBI dbEST/CGAP (Emmert-Buck et al., *Science* 274:998-1101 (1996); Krizman, D. B. et al., *Cancer Res.* 56:5380-5383 (1996); Strausberg, R. L. et al., *Nat. Genet.* 16:415-516 (1997)) as of Apr. 25, 1998, which included 1,001,294 ESTs in 656 different libraries. The majority of the ESTs (>650,000 ESTs, >64% of the total ESTs) came from Soares libraries and/or the NCI Cancer Genome Anatomy Project (CGAP).

Our EST database clustering and filtering program, originally designed to identify genes that are very specifically expressed in prostate and prostate cancer (Vasmatzis, G. et al., *Proc. Natl. Acad. Sci., USA* 95:300-304 (1998)) was updated with the additional EST data. We "relaxed" the specificity requirement for the selection of potentially useful EST clusters because we observed candidate genes on our search list which were not entirely prostate specific, that might still be acceptable and useful as targets for the diagnosis or therapy of prostate cancer. For example, EST clusters which show several "expression-hits" in non-prostate/cancer tissues are still interesting if the non-prostate expression specificity is found in libraries other than prostate that come from tumors or nonessential tissues. Therefore, in selecting candidates for further, experimental processing, we "tolerated" the occurrence of ESTs from candidate clusters in a limited number of normal tissues. These were placenta, other gender specific tissues and fetal tissues. In identifying target antigens for tumor therapy, the expression of a gene in more than one type of tumor is not an impediment to the applicability of such targets; in fact it may be desirable because expression of a given protein in multiple tumors will broaden the application of reagents that are developed based upon such targets. The expression of "tumor"-proteins in certain normal tissues may be neglected if the expression is in reproductive tissues. Expression in uterus, ovary or placenta is not relevant for males, and prostate or testis expression is not relevant for females.

The output of our recent database analysis is a list of clones that occur frequently in prostate, prostate cancer, as well as in other tumors, and that may also be present in some normal tissues. We sorted this list according to EST-frequency in prostate and prostate tumors. Since the EST frequency in libraries of defined tissues approximately correlates with the level of tissue specific expression of the corresponding gene, this tissue-specific ranking may identify genes that are preferentially expressed in prostate and prostate cancer.

Figure 3:
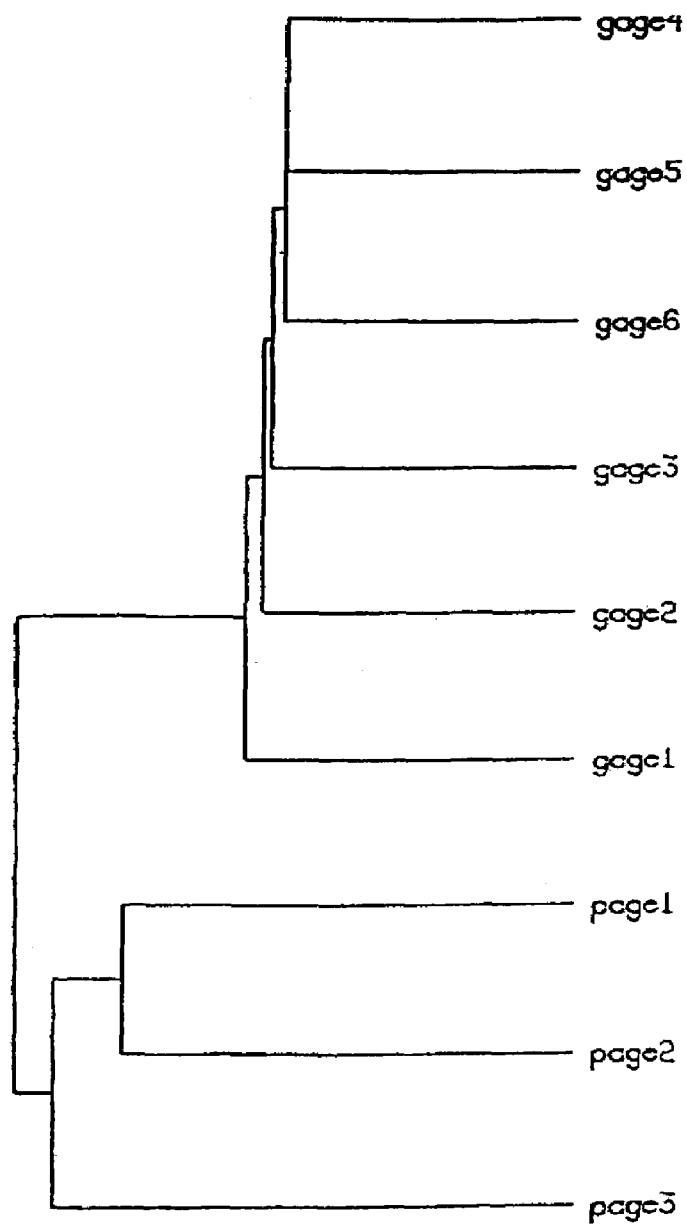
FIG. 3: Relation of the sequences of MAGE, GAGE, PAGE and other so far uncharacterized EST clusters: The GCG program "PILEUP" was used to compare the multiple protein sequences of the GAGE and PAGE protein family. The dendrogram shows that PAGE proteins are a separate group of proteins that are less related to GAGE proteins.

B. Detection of a cDNA Cluster that Encodes a X-Linked Gage Like Protein Predominantly Represented in Prostate and Prostate Cancer Libraries One of the cDNA clusters present on the database search list was observed to be preferentially present in prostate and prostate tumor libraries, and additionally, in placenta and in a mixed pooled library which contained mRNA from uterus. The computational analysis portion of Table 1 lists the distribution of individual EST sequences that correspond to this cDNA cluster in several different EST libraries. ESTs from this cluster are most abundantly found in libraries from prostate and prostate cancer where they represent 0.022% (prostate) and 0.031% (prostate cancer) of the total cDNA sequence population. They were also represented in placenta libraries (0.016%) and in a library pool that contained cDNA from uterus (0.013%). Homology analyses showed that the sequence of this cDNA cluster is similar to a family of GAGE like proteins (Van den Eynde et al., *J. Exp. Med.* 182:689-698 (1995); Lucas, S. et al., *Cancer Res.* 4:743-752 (1998); Old, L. J. et al., *J. Exp. Med.* 187:1163-1167 (1998)). An alignment of the protein sequence that is predicted from its reading frame with the sequences of members of the GAGE family is shown in FIG. 1A. The homology to GAGE is highly significant but it is not as pronounced as that of the other GAGE proteins to each other, and we observed some weaker similarity to MAGE proteins (Old, L. J. et al., *J. Exp. Med.* 187:1163-1167 (1998); van der Bruggen, P. et al., *Science* 254:1643-1647 (1991); Stockert, E., Jäger, E. et al., *J. Exp. Med.* 187:1349-1354 (1998); De Plaen, E., et al. *Immunogentics* 40:360-369 (1994); Takahashi K., et al., *Cancer Res.* 55:3478-3482 (1995); Boel, P. et al., *Immunity* 2:167-175 (1995)). Because this novel member of the MAGE/GAGE protein family appears to be strongly expressed in prostate and placenta we named it PAGE-4. Further database searches identified additional EST clusters with significant similarity to PAGE-4 and less similarity to GAGE and MAGE. This suggests that PAGE-4 is a member of a family of related proteins like MAGE and GAGE. An alignment of PAGE-4 with sequences of PAGE-2 (predominantly in testis) and PAGE-3 (one EST from a pooled, testis containing library) is shown in FIG. 1. In addition, we identified several other EST clusters with homology to PAGE as well as to GAGE, but which do not have the striking similarities that the other GAGE family members have to each other. Representatives of some of these cDNA clusters are the ESTS yd88e11 (fetal liver/spleen), yw86a06 (placenta) and yi21h01 (placenta). The relation of the sequences of GAGE and PAGE is shown in a graph form (dendrogram) in FIG. 3. There are two sequence stretches in PAGE-4 that contain Arg-Gly-Asp (RGD) motifs, and the surrounding sequence is similar to a RGD containing sequence present in the metabotropic glutamate receptor 6 (Hashimoto, T. et al., *Eur. J. Neurosci.* 9:1226-1235 (1997)). RGD motifs are frequently found in cell adhesion proteins, and it has been suggested that RGD sequences in several receptor molecules are involved in cell-cell interactions (Papadopoulos, G. K. et al., *Int. J. Biol. Macromol.* 1:51-57 (1998)).

Several GAGE/MAGE like proteins have recently been described as CT antigens, i.e., proteins that are expressed preferentially in cancers and testis (Old, L. J. et al., *J. Exp. Med.* 187:1163-1167 (1998); van der Bruggen, P. et al., *Science* 254:1643-1647 (1991); Stockert, E., Jäger, E. et al., *J. Exp. Med.* 187:1349-1354 (1998); De Plaen, E., et al. *Immunogentics* 40:360-369 (1994); Takahashi, K., et al., *Cancer Res.* 55:3478-3482 (1995); Boel, P. et al., *Immunity* 2:167-175 (1995)). It has been shown that many MAGE genes are positioned in at least two clusters on the human X chromosome (Lucas, S. et al., *Cancer Res.* 4:743-752 (1998); Old, L. J. et al., *J. Exp. Med.* 187:1163-1167 (1998); Lurquin, C. et al., *Genomics* 3:397-408 (1997); Muscatelli, F. et al., *Proc. Natl. Acad. Sci. USA* 92:4987-4991 (1995)). We have found, by radioactive hybridization of a Somatic Cell Hybrid Southern blot, that the PAGE-4 gene is also located on the X-chromosome (data not show). A recent database deposit of mapped X chromosomal transcript sequences confirms the X chromosome mapping of PAGE-4 and places PAGE-4 at position Xp11.23 (Strom, T. M. et al., Genbank AJ005894 (1998)).

C. PAGE-4 is Expressed in Normal Prostate, Testis, Uterus, Fallopian Tube and Placenta, and in Prostate and Uterine Cancers.

Figure 2B:
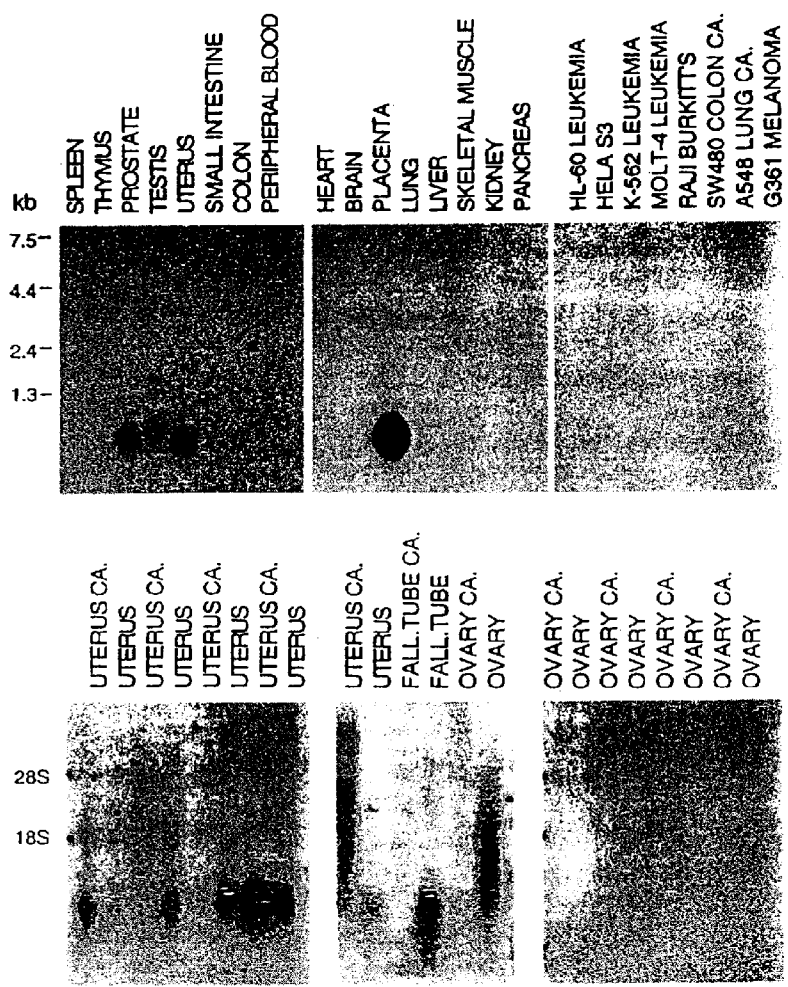
Figure 2C:
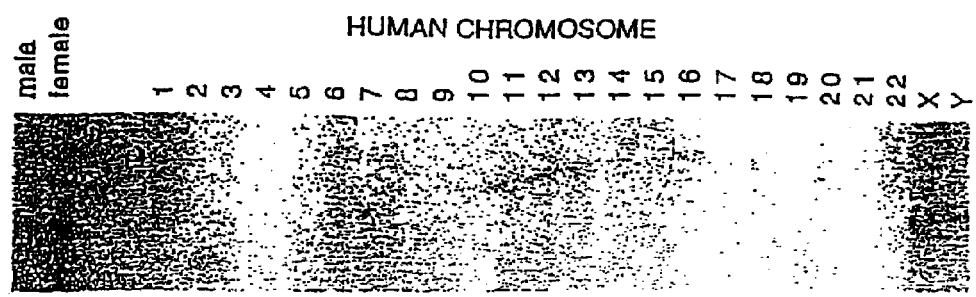

To evaluate experimentally the specificity of expression of PAGE-4, which was suggested by the database analysis to be expressed preferentially in prostate and prostate tumors, we hybridized Dot blots and Northern blots of mRNAs from different tissues with a radioactive labeled PAGE-4 probe. The results of these experiments, which were done with a 140 bp probe under very stringent hybridization conditions, are shown in FIG. 2 and summarized in Table 1. Dot blot hybridizations (FIG. 2A) show a significant level of PAGE-4 expression in normal prostate. We also found weaker expression in testis, and very strong expression in normal placenta. Additional signals were observed in uterus and a very weak signal in ovary. The very strong placental expression which was stronger than prostate and the expression in ovary and testis was not predicted from the results of the database analysis. The expression in uterus is congruent with the appearance of PAGE-4 ESTs in a library that was derived from pooled mRNAs, including uterus. Among the 58 normal tissues and cancer cell lines that we tested, only prostate, testis, placenta, uterus and ovary showed PAGE-4 hybridization signals in dot blots. The signal with ovary was very weak in Dot blots.

In Northern blots, prostate, testis, placenta and uterus, but none of the other tissues, displayed a clear ~500 b band that hybridized with the PAGE-4 probe (FIG. 2A). Further analyses of Northern blots with mRNA preparations from different uterine cancer samples showed that PAGE-4 is in uterine cancers. FIG. 2B (first panel) is a Northern blot containing total RNA from different uterine tumors (lns. 1, 3, 5, 7) and corresponding normal uterus (lns. 2, 4, 6, 8). The PAGE-4 signal is apparent in all normal uterus and uterine cancer samples; and in some instances the PAGE-4 signal in mRNA from uterine cancer is stronger than in the adjacent normal tissue (FIG. 2 B). On the other hand, expression of PAGE-4 in ovary, which we tested because of the weak dotblot hybridization signal, could not be confirmed. FIG. 2B ($3^{rd}$ panel) shows that Northern blots containing mRNA from ovarian cancer and adjacent normal ovary showed no evidence of PAGE-4 expression; however we did find PAGE-4 in mRNA from normal fallopian tube (FIG. 2B, middle panel).

Figure 4:
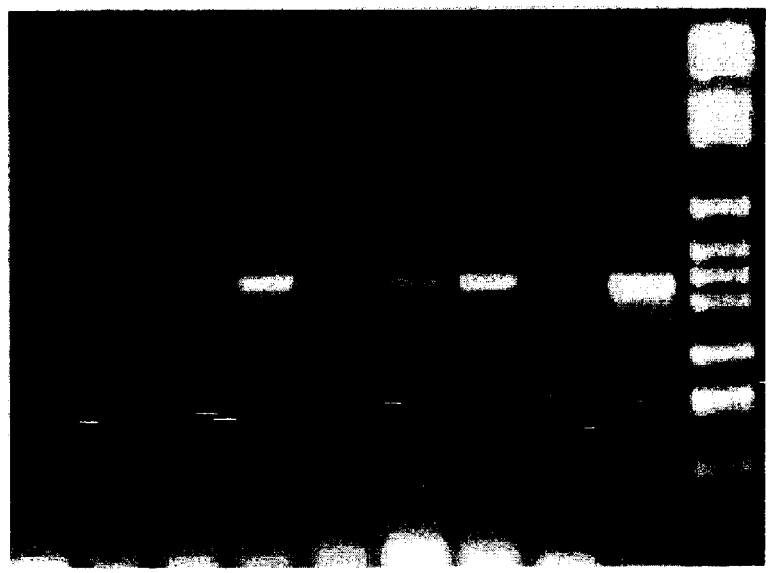
FIG. 4: RT-PCR analysis of PAGE-4 expression: Ethidium bromide stained 2.5% agarose gel; PAGE-4 cDNA was amplified with 5' and 3'-end specific PAGE primers (40 cycles 94° C.-58° C.-72° C., 1 min each).

To confirm the presence of PAGE-4 transcripts experimentally in malignant prostate we analyzed a prostate cancer cDNA preparation (from Invitrogen) by RT-PCR with primers that specifically amplify a full length PAGE-4 cDNA fragment. FIG. 4 shows that PAGE-4 mRNA can be detected by PCR in cDNA samples from malignant prostate, as well as in normal prostate and in a testicular tumor. The PAGE-4 fragment was also obtained by PCR from a placental cDNA library, but not from libraries from human muscle or liver. In the prostate tumor cell lines LnCAP and PC3, PAGE-4 expression could be detected by hybridization analyses of RT-PCR products (data not shown) but not by Northern blots or RT-PCR using ethidium-bromide stained agarose gels. These experimental observations, combined with the fact that PAGE-4 is present in CGAP cDNA libraries derived from different prostate cancers (Table 1), indicates that PAGE-4 is predominantly expressed in normal and neoplastic male and female reproductive tissues and particularly in prostate, testis and uterus.

IV. Significance of the PAGE-4 Gene

PAGE-4 is a human X-linked gene that is strongly expressed in prostate and prostate cancer, but is also expressed in other male and female reproductive tissues: testis, fallopian tube, placenta, uterus and uterine cancer. PAGE-4 shows similarity with the GAGE protein family, but it diverges significantly from members of the family so that it appears to belong to a separate family. This, and the existence of other genes, PAGE-2 and PAGE-3, that share more homology with PAGE-4 than with members of the GAGE family indicates that the PAGE proteins constitute a separate protein family.

The specificity of PAGE-4 expression in normal and malignant tissues that are associated with male and female reproductive function coincides with the localization of this gene on the X chromosome. This observation provides a link between sex-chromosomal genes and reproductive functions. For example, it is known that a testis defining gene (SRY) is located on the Y chromosome (McElreavey, K. et al., *Heredity* 6:599-611 (1995)), and other sex determining genes are predicted to be positioned on the X chromosome (Ogata T. et al., *Acta Paediatr Jpn,* 4: 390-398 (1996); Dabovi, B. et al., *Mamm Genome* 9:571-580 (1995)). The family of MAGE proteins is located on Xp21 and Xp28 and is expressed in testis and tumors. PAGE-4 also is located on the X chromosome and is expressed in male as well as female specific tissues. It is interesting to speculate that MAGE and/or PAGE proteins are involved in sex determination. One important question in this context is in which cells of the reproductive tissues PAGE-4 is expressed. Because of the high homology of the various members of the GAGE family, this question can probably not be solved by in situ hybridizations, but instead specific antibodies will be required. The presence of PAGE-4

ESTs in microdissected CGAP tumor libraries suggests that PAGE-4 is probably expressed in the epithelial cells from which most tumors originate.

V. Uses of the PAGE-4 Protein and Gene

In addition to the interesting basic questions about the molecular function of PAGE such as its cellular localization and the function of the RGD sequences, the expression pattern of PAGE-4 opens the possibility of its usefulness in tumor diagnosis and in therapy. In males, PAGE-4 is found in prostate and testis, as well as in prostate and testicular cancer. Obviously, expression in placenta, fallopian tube or uterus is irrelevant for therapy of males. Conversely, testicular and prostate expression can be neglected in females, as well as the high expression in normal placenta.

In an important group of embodiments, all or part of the PAGE-4 gene product can be used as a vaccine to enhance the immune system's ability to eliminate PAGE-4 containing cells (Old, L. J. et al., *J. Exp. Med.* 187:1163-1167 (1998); van der Bruggen, P. et al., *Science* 254:1643-1647 (1991); Stockert, E., Jäger, E. et al., *J. Exp. Med.* 187:1349-1354 (1998); De Plaen, E., et al. *Immunogenetics* 40:360-369 (1994); Takahashi, K., et al., *Cancer Res.* 55:3478-3482 (1995); Boel, P. et al., *Immunity* 2:167-175 (1995)). The relation to MAGE and GAGE proteins strongly suggests that PAGE-4 is processed or presented by cells, and thus is suitable as a vaccine, (Old, L. J. et al., *J. Exp. Med.* 187:1163-1167 (1998); van der Bruggen, P. et al., *Science* 254:1643-1647 (1991); Stockert, E., Jäger, E. et al., *J. Exp. Med.* 187:1349-1354 (1998); De Plaen, E., et al. *Immunogentics* 40:360-369 (1994); Takahashi, K., et al., *Cancer Res.* 55:3478-3482 (1995); Boel, P. et al., *Immunity* 2:167-175 (1995)).

Many approaches to vaccination are known in the art. One preferred option is direct vaccination with plasmid DNA (Donnelly, J. J. et al., *Annu. Rev. Immunol.* 15:617-648 (1997)). We are able to obtain good expression of PAGE-4 protein with mammalian expression plasmids (data not shown), and it has been demonstrated that DNA-immunization with such expression constructs leads to good immune responses (Donnelly, J. J. et al., *Annu. Rev. Immunol.* 15:617-648 (1997); Chowdhury, P. et al., *Proc. Natl. Sci USA* 95:669-674 (1998)). Therefore, this method should generate anti-PAGE-4 responses, and allow us to demonstrate that "PAGE-4-vaccination" can eliminate PAGE-4 expressing cells, as a therapeutic approach towards neoplasms of the prostate, testis and uterus.

In some embodiments, only an immunogenic portion of the PAGE-4 protein is used in forming the vaccine. Methods of determining immunogenic portions of a protein and selecting appropriate peptides which can activate T-cell responses to an antigen of interest are known in the art.

The specific detection of PAGE-4 is expected to be valuable for the diagnosis of prostate and testicular tumors, as well as uterine tumors. There are sufficient differences between PAGE-4 and other members of the PAGE and MAGE antibodies to produce specific antibodies, and we have demonstrated the production of PAGE-4 antibodies. Analyses with such antibodies is expected to confirm by immunohistology the expression specificity that is seen in database and mRNA analyses. The antibodies can also be used to detect the presence of PAGE-4 in biological samples. In in vitro applications, the antibodies can be used in any of a number of standard immunoassays. For example, the sample can be contacted with mouse anti-PAGE-4 antibody, washed with buffer, and tested for the presence of bound antibody using a goat anti-mouse antibody (antisera from a goat which recognizes mouse antigens). Alternatively, the presence of PAGE-4 can be determined by detecting the presence of mRNA encoding PAGE-4 through PCR or any of several other assays known in the art.

Since removal of normal prostate, testis or uterine tissue, together with the cancerous lesions, is part of standard cancer therapy, the detection of PAGE-4 in body tissues following removal of the lesions and of the organs expected to express PAGE-4 indicates that not all of the cancerous tissue has been removed. Accordingly, detection of PAGE-4 protein can be a valuable signal that further steps may be needed to eliminate the cancer.

Specific targeting and elimination of PAGE-4 positive normal and malignant tissue is expected to be a promising therapeutic approach. In one embodiment, ligands to PAGE-4, or to portions of PAGE-4 expressed in conjunction with MHC molecules, are used to target therapeutic agents to cells or tissues expressing PAGE-4. For example, anti-PAGE-4 antibodies can be coupled to conventional chemotherapeutic agents to deliver them specifically to PAGE-4 containing cells, thus providing a high local concentration of the agent while reducing the agent's systemic effect. Anti-PAGE-4 antibodies can also be coupled to and used to deliver other therapeutic agents, such as radioisotopes or plant or bacterial cytotoxins. The antibody portion of the molecule acts as a targeting moiety and delivers the toxin to the cell recognized by the antibody. The toxin, in turn, is engineered to lack portions responsible for non-specific binding so that it affects primarily only those cells to which it is delivered by the targeting moiety.

In another embodiment, nucleic acids which are complementary to RNA encoding PAGE-4 can be administered to a patient in need. The use of synthetic oligonucleotides to bind to mRNA in a sequence-specific manner has been found to block translation of the encoded protein. Protocols for a number of clinical trials for systemic administration of antisense oligonucleotides directed against a variety of conditions are available in the literature and provide those of skill in the art guidance on, among other things, the construction of appropriate synthetic oligonucleotides, the design of preclinical and clinical studies, methods of administering such oligonucleotides to patients, and other information relevant to use of antisense oligonucleotides as therapeutic agents. See, e.g., Yacyshyn, Gastroenterology, 114:1133-1142 (1998); Bishop, *J. Clin. Oncol.*, 14:1320-1326 (1996); Morgan, Human Gene Ther. 7:1281-1306 (1996); Bayever, Antisense Res Devel, 3:383-390 (1993). See also, Zon, Molec. Nueurobiol. 10:219-229 (1995). At least one antisense drug has been approved by the FDA.

VI. Vaccine Strategies

A. Determination of Immunogenic Peptides

CTL response is based on the presentation to CD8+ T cells of antigens in combination with molecules of HLA class I. One difficulty in vaccine design has been the polymorphic nature of HLA class I molecules, of which more than 100 alleles and isotypes are known. In humans, MHC class I antigens are encoded by the HLA-A, B, and C loci. HLA-A and B are expressed at the cell surface in roughly equal densities, whereas HLA-C is expressed as significantly lower density. Each of these loci has numerous alleles.

For peptide based vaccines, it is preferable if the peptides comprise motifs recognized by alleles having a wide distribution in the human population. Since the MHC alleles occur at different frequencies within different ethnic groups and races, the choice of target MHC may depend upon the target population. For example, the majority of the Caucasoid population can be covered by peptides which bind to four HLA allele subtypes, HLA-A2.1, A1, A3.2, and A24.1, while adding peptides binding to a first allele, HLA-A11.2, encompasses the majority of the Asian population. See, e.g., International Publication No. WO 94/20127; Sidney, J., et al., "Broadly Reactive HLA Restricted T Cell Epitopes and their Implications for Vaccine Design," in Kaufmann, ed, *Concepts in Vaccine Design* (Walter de Gruyter, Berlin, 1996).

Analysis of numerous alleles has also permitted characterization of the alleles by "supertypes," which recognize antigen presented for recognition by the presence of certain amino acids or types of amino acids in certain positions. For example, the B7-like supertype recognizes proline in position 2 and hydrophobic or aliphatic amino acids at the C-terminus, whereas the A3-like supertype is defined by a shared preference for peptides bearing (in single letter code) A, L, I, V, M, S, or T at position 2 and a positively charged residue at the C-terminus. See, Sidney, supra. Binding motifs for alleles HLA-A1, A2.1, A3.2, A11.2, and A24, for example, are well characterized (see, e.g., Rammensee, et al., Ann. Rev. Immun. 11:213-244 (1993); Ruppert, et al., Cell, 74:929-937 (1993); Kubo, et al., J. Immun., 152:3913-3924 (1994)); these alleles are expressed in 90% of the Caucasian population. In fact, the "sequence motifs" and "anchor residues of the various MHC alleles have been analyzed in detail and hundreds of peptide ligands for the more important class I molecules have been reported (reviewed in Rammensee, H-G., et al., Immunogenetics, 41:178-228 (1995) ("Rammensee, 1995")). Rammensee, 1995 sets forth for each allele the "anchor" residues at positions 2 and 9, any auxiliary anchor positions for the particular allele, and preferred residues at other positions.

The selection and screening of peptide epitopes for their MHC binding capacity and in vitro and in vivo activation of CTLs has also been closely studied and is taught in the literature. See e.g., Celis, E., et al., Cancer Biol., 6:329-336 (1995); Chesnut, R., et al., "Design and Testing of Peptide-Based Cytotoxic T-Cell Mediated Immunotherapeutics to Treat Infectious Diseases and Cancer," in Powell, M. and Newman, M., eds., *Vaccine Design: The Subunit and Adjuvant Approach* (Plenum Press, New York, 1995); Celis, E., et al., Mol. Immunol., 31:1423-1430 (1994) (hereafter, "Celis, 1994"); Lanzavecchia, A. Science, 260:937-943 (1993); Celis, E., et al., Proc Natl Acad Sci USA 91:2105-2109 (1994); Sinigaglia, F., and Hammer, J., J. Exp. Med. 181:449-451 (1995).

For example, Celis, et al., Mol. Immun. 31:1423-1430 (1994) ("Celis, 1994"), describes the identification of potential CTL epitopes of MAGE-1. They screened the 309 amino acid sequence of the MAGE-1 protein for the presence of peptides 9-10 residues in length, containing binding motifs for HLA-A1, -A2.1, -A3.2, -A11, and A24, and synthesized 170 such peptides. The peptides were tested for their binding to purified MHC molecules by standard assays and those with high or intermediate affinity to the purified MHC molecules selected as potential epitopes for melanoma-specific CTL. Peptides so selected are then candidates for testing for their ability to activate CTLs. A variety of assays for this purpose are known in the art, and include immunization of transgenic mice, in vitro CTL studies using PBMC or tumor infiltrating lymphocytes isolated from patients with cancers of the relevant type, and in vitro inductions using PBMC from normal HLA-typed individuals. See, e.g., Celis, 1994; Vitiello, et al., J. Exp. Med., 173:1007-1015 (1991); Traversari, et al., J. Exp. Med., 176:1453-1457 (1992); Celis, et al., Proc Natl Acad Sci USA, 91:2105-2109 (1994). The tumor associated antigens MAGE-2 and MAGE-3 have also been used as the basis for the development of 9-mer and 10-mer synthetic peptides which bind to a chosen HLA allele and which stimulate CTLs against those antigens. See, U.S. Pat. No. 5,662,907.

Recent studies and advances in combinatorial peptide chemistry have improved the ability to describe and to predict the specificities of HLA molecules. See, e.g., Buus, S., Curr. Opin. Immunol., 11:209-213 (1999); Schafer, J., et al., Vaccine, 16:1880-1884 (1998). Additional methods for predicting whether a particular peptide will bind to a MHC molecule have been developed and have been asserted to be more accurate than the use of sequence motifs. For example, Gulukota. K., et al., J. Mol. Biol., 267:1258-1267 (1997), teach what they style as neural net and polynomial methods for predicting whether a particular peptide will bind to a MHC molecule. The methods are complementary, with one eliminating false positives and the other better at eliminating false negatives.

B. Vaccines of the Invention

The present invention provides the recognition that the PAGE-4 protein is expressed in cancers, especially those of the prostate, testicles, and uterus. As noted in the preceding sections, the relation to MAGE and GAGE proteins strongly suggests that PAGE-4 is processed or presented by cells, and thus is suitable as a vaccine. The PAGE-4 protein itself can be used as a therapeutic vaccine to enhance the patient's own immune response to tumor cells expressing PAGE-4. The vaccine, which acts as an immunogen, may be a cell, a lysate from cells transfected with a recombinant expression vector, or a culture supernatant containing the expressed protein. Alternatively, the immunogen can be a partially or substantially purified recombinant PAGE-4 protein.

In an important class of embodiments, the immunogen is a PAGE-4 peptide or analog thereof. As noted in the preceding section, HLA alleles bind 9-mer or 10-mer amino acid sequences, but different alleles preferentially bind particular amino acids at particular positions. In most cases, high affinity peptides are immunogenic. See, e.g., Sette, et al., J. Immunol., 153:5586-5592 (1994). Using the art-recognized sequence motifs, neural net and polynomial methods discussed above, one of skill can readily select sequences of the PAGE-4 protein which have high affinity for alleles which are found in any given target human population. Given the relation of PAGE-4 to MAGE proteins, it is expected that the procedure used by Celis, 1994 to identify CTL epitopes for MAGE-1 and the procedures employed by Kubo, et al., to find synthetic peptides activating CTLs against MAGE-2 and MAGE-3 (as taught in U.S. Pat. No. 5,662,907), can be employed to find and test potential CTL epitopes for PAGE-4.

The identification of motifs can be performed manually, or by computer, using programs such as the "FINDPATTERNS" program reported by Devereux et al., Nucl. Acids Res., 12:387-395 (1984). The peptides will typically be between 7 and 30 amino acids in length, are preferably between 8 and 20 amino acids in length, and more preferably are between 8 and 15 amino acids in length. Most preferably, the peptides are 9 or 10 amino acids in length, and correspond to the length most useful for the particular allele to which they are intended to bind. Typically, the peptides are selected because they satisfy the binding preferences of one or more MHC alleles found in a desired percentage of the target population. The peptides selected can readily be tested for binding to an HLA allele of choice and for activation of cytotoxic T lymphocytes by the assays mentioned above (see, e.g., U.S. Pat. No. 5,662,907).

As noted, each allele has certain preferred residues at certain positions. Thus, the binding affinity of a particular peptide for a particular allele can in some cases be improved by making a substitution of a preferred amino acid for the one present in the native sequence of the original protein. The peptide can then be tested by the assays discussed above to determine its binding ability and to see if it retains the ability to induce a CTL response against cells expressing the PAGE-4 protein.

Modified peptides or analogs thereof can also be substituted for the natural amino acids to impart desired characteristics to the immunogenic peptide. The modification can be, for example, the substitution of L-amino acids by their D-isomers, or by derivatized L-amino acids. Further descriptions of substitutions and modifications are disclosed in, for example, International Publication Nos. WO 94/20127 and WO 95/25122. The proteins or peptides may be conjugated with other agents to increase their immunogenicity or half-life in the body, or both. In some embodiments, the peptides or proteins are conjugated to lipid or lipoprotein or administered in liposomal form or with adjuvant. Lipidation of the peptides or proteins, and appropriate adjuvants, are discussed in the section on pharmaceutical compositions, infra.

While the immunogenic peptides or proteins may be administered in a pure or substantially pure form, it is generally preferable to present them as a pharmaceutical composition, formulation or preparation. In the case of nucleic acids, however, "naked" DNA (typically, DNA in a plasmid with a strong promoter) can be introduced. See, e.g., Rappuoli and Del Giudice, "Identification of Vaccine Targets," in Paoletti and McInnes, eds., *Vaccines, From Concept to Clinic*, CRC Press, Boca Raton, Fla. (1999). These authors state that vaccination by naked DNA is the most effective method known to date for inducing a cytotoxic immune response against an antigen. Id. In a preferred embodiment, the nucleic acids are loaded onto gold microcarriers, which are then introduced through the skin by a pulse of helium via the Helios™ Gene Gun (Bio-Rad Laboratories, Inc., Hercules, Calif.).

VI. Ex Vivo Uses of the Peptides or Protein

The compositions and methods of the invention can be used ex vivo to augment an organism's immune response. In this regard, a portion of the organism's lymphocytes are removed and cultured in vitro with high doses of the immunogenic peptides or the PAGE-4 protein, providing a stimulatory concentration of peptide in the cell medium in excess of that which could be achieved in the body. Following treatment to stimulate the CTLs, the cells are returned to the host, allowing the activated CTLs to attack PAGE-4-expressing cells in the organism.

In one method, CTL responses to PAGE-4-expressing cells are induced by incubating in tissue culture a patient's CTL precursor cells together with a source of antigen presenting cells and the appropriate immunogenic peptide or the PAGE-4 protein. After an appropriate incubation period (which may be 1-4 weeks), the CTL precursors are activated and mature and expand into CTLs. To optimize in vitro conditions, the culture of stimulator cells is typically maintained in an appropriate serum-free medium. Peripheral blood lymphocytes are conveniently isolated following simple venipuncture or leukopheresis of normal donors or patients and used as the responder cell sources of CTL precursors. In one embodiment, the appropriate APC are incubated with about 10-100 μM of peptide in serum-free media for 4 hours under appropriate culture conditions. The peptide-loaded APC are then incubated with the responder cell populations in vitro for 5 to 10 days under optimized culture conditions.

Positive CTL activation can be determined by assaying the cultures for the presence of CTLs that kill radiolabeled target cells, both specific peptide-pulsed targets as well as target cells expressing endogenously processed form of the PAGE-4 protein from which the peptide sequence was derived. Specificity and MHC restriction of the CTL of a patient can be determined by a number of methods known in the art. For instance, CTL restriction can be determined by testing against different peptide target cells expressing appropriate or inappropriate human MHC class I. The peptides that test positive in the MHC binding assays and give rise to specific CTL responses are identified as immunogenic peptides. More details about the selection of CTLs and their separation from antigen presenting cells are set forth in, e.g., U.S. Pat. No. 5,932,224. See also; WO 95/25122.

Antigen presenting cells may also be exposed to vectors carrying nucleic acid sequences encoding the immunogenic peptides or the PAGE-4 protein, or "naked" DNA encoding the peptides or proteins can be introduced by the Helios™ Gene Gun (see previous section) or other methods. Once dosed or transfected, the cells may be propagated in vitro or returned to the patient. Conveniently, the cells are propagated in vitro until they reach a predetermined cell density, after which they are reintroduced into the host.

Return of cells to the host may be by any of several methods well known in the art, and include procedures such as those exemplified in U.S. Pat. No. 4,844,893 to Honsik and U.S. Pat. No. 4,690,915 to Rosenberg. Conveniently, the cells may be reintroduced by intravenous infusion.

VII. Antibody Production

Methods of producing polyclonal antibodies are known to those of skill in the art. In brief, an immunogen, preferably isolated PAGE-4 protein or immunogenic peptides thereof are mixed with an adjuvant and animals are immunized with the mixture. When appropriately high titers of antibody to the immunogen are obtained, blood is collected from the animal and antisera are prepared. If desired, further fractionation of the antisera to enrich for antibodies reactive to the polypeptide is performed. See, e.g., Coligan, CURRENT PROTOCOLS IN IMMUNOLOGY, Wiley/Greene, NY (1991); and Harlow & Lane, supra, which are incorporated herein by reference.

Monoclonal antibodies may be obtained by various techniques familiar to those skilled in the art. Description of techniques for preparing such monoclonal antibodies may be found in, e.g., Stites, et al. (eds.) BASIC AND CLINICAL IMMUNOLOGY (4TH ED.), Lange Medical Publications, Los Altos, Calif., and references cited therein; Harlow & Lane, supra; Goding, MONOCLONAL ANTIBODIES: PRINCIPLES AND PRACTICE (2D ED.), Academic Press, New York, N.Y. (1986); Kohler & Milstein, *Nature* 256:495-497 (1975); and particularly Chowdhury, P. S., et al., *Mol. Immunol.* 34:9 (1997), which discusses one method of generating monoclonal antibodies.

It is preferred here that monoclonal antibodies are made by immunizing an animal with a nucleic acid sequence that encodes the desired immunogen, in this case, PAGE-4. Immunization with non-replicating transcription units that encode heterologous protein(s) elicits antigen specific immune responses. After translation into the foreign protein, the protein is processed and presented to the immune system like other cellular proteins. Because it is foreign, an immune response is mounted against the protein and peptide epitopes that are derived from it (Donnelly, et al., *J. Immunol. Methods* 176:145-152 (1994); and Boyer, et al., *J. Med. Primatol.* 25:242-250 (1996)). This technique has two significant advantages over protein-based immunization. One is that it does not require the purification of the protein, which at best, is time consuming and in cases of many membrane proteins, is very difficult. A second advantage is that since the immunogen is synthesized in a mammalian host, it undergoes proper post-translational modifications and folds into the native structure.

In preferred embodiments, the monoclonal antibody is a scFv. Methods of making scFv antibodies have been described. See, Huse, et al., supra; Ward, et al. *Nature* 341: 544-546 (1989); and Vaughan, et al., supra. In brief, mRNA from B-cells is isolated and cDNA is prepared. The cDNA is amplified by well known techniques, such as PCR, with primers specific for the variable regions of heavy and light chains of immunoglobulins. The PCR products are purified by, for example, agarose gel electrophoresis, and the nucleic acid sequences are joined. If a linker peptide is desired, nucleic acid sequences that encode the peptide are inserted between the heavy and light chain nucleic acid sequences. The sequences can be joined by techniques known in the art, such as blunt end ligation, insertion of restriction sites at the ends of the PCR products or by splicing by overlap extension (Chowdhury, et al., *Mol. Immunol.* 34:9 (1997)). After amplification, the nucleic acid which encodes the scFv is inserted into a vector, again by techniques well known in the art. Preferably, the vector is capable of replicating in prokaryotes and of being expressed in both eukaryotes and prokaryotes.

In a particularly preferred embodiment, scFv are chosen through a phage display library. After antibody titers against the antigen in the immunized animal reach their maximum, the animal is sacrificed and the spleen removed. The procedure described above for synthesizing scFv is followed. After amplification by PCR, the scFv nucleic acid sequences are fused in frame with gene III (gIII) which encodes the minor surface protein gIIIp of the filamentous phage (Marks, et al., *J. Biol. Chem.* 267:16007-16010 (1992); Marks, et al., *Behring Inst. Mitt.* 91:6-12 (1992); and Brinkmann, et al., *J. Immunol. Methods* 182:41-50 (1995)). The phage express the resulting fusion protein on their surface. Since the proteins on the surface of the phage are functional, phage bearing PAGE-4-binding antibodies can be separated from non-binding or lower affinity phage by panning or antigen affinity chromatography (McCafferty, et al., *Nature* 348:552-554 (1990)).

In a preferred embodiment, scFv that specifically bind to PAGE-4 protein or immunogenic peptides thereof are found by panning. Panning is done by coating a solid surface with PAGE-4 protein or an immunogenic peptide thereof and incubating the phage on the surface for a suitable time under suitable conditions. The unbound phage are washed off the solid surface and the bound phage are eluted. Finding the antibody with the highest affinity is dictated by the efficiency of the selection process and depends on the number of clones that can be screened and the stringency with which it is done. Typically, higher stringency corresponds to more selective panning. However, if the conditions are too stringent, the phage will not bind. After one round of panning, the phage that bind to PAGE-4 or immunogenic peptide coated plates are expanded in *E. coli* and subjected to another round of panning. In this way, an enrichment of 2000-fold occurs in 3 rounds of panning. Thus, even when enrichment in each round is low, multiple rounds of panning will lead to the isolation of rare phage and the genetic material contained within which encodes the sequence of the highest affinity antibody. The physical link between genotype and phenotype provided by phage display makes it possible to test every member of a cDNA library for binding to antigen, even with libraries as large as 100,000,000 clones.

VIII. Production of Immunoconjugates

Immunoconjugates include, but are not limited to, molecules in which there is a covalent linkage of an effector moiety, such as a therapeutic agent, to an antibody. A therapeutic agent is an agent with a particular biological activity directed against a particular target molecule or a cell bearing a target molecule. One of skill in the art will appreciate that therapeutic agents may include various drugs such as vinblastine, daunomycin and the like, cytotoxins such as native or modified *Pseudomonas* exotoxin or Diphtheria toxin, encapsulating agents, (e.g., liposomes) which themselves contain pharmacological compositions, radioactive agents such as $^{125}H$, $^{32}P$, $^{14}C$, $^{3}H$ and $^{35}S$ and other labels, target moieties and ligands.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

In preferred embodiments, the cell growth-inhibiting molecules of the invention are prepared by cloning techniques. Examples of appropriate cloning and sequencing techniques, and instructions sufficient to direct persons of skill through many cloning exercises are found in Sambrook, et al. MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill. Nucleic acids encoding native effector molecules or anti-PAGE-4 antibodies can be modified to form the effector molecule, antibodies, or immunoconjugates of the present invention. Modification by site-directed mutagenesis is well known in the art. Nucleic acids encoding effector molecule or anti-PAGE-4 antibodies can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an anti-PAGE-4 scFv antibody into a vector which comprises the cDNA encoding the effector molecule. The insertion is made so that the scFv and the EM are read in frame, that is in one continuous polypeptide which contains a functional Fv region and a functional EM region. In a particularly preferred embodiment, cDNA encoding a diphtheria toxin fragment is ligated to a scFv so that the toxin is located at the carboxyl terminus of the scFv. In a most preferred embodiment, cDNA encoding PE is ligated to a scFv so that the toxin is located at the amino terminus of the scFv.

In addition to recombinant methods, the immunoconjugates, effector molecules, and antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963); and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicyclohexylcarbodiimide) are known to those of skill.

Once the nucleic acids encoding an EM, anti-PAGE-4 antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment electroporation or lipofection for mammalian cells. Cells transformed by the cassettes can be selected by resistance to antibiotics conferred by genes contained in the cassettes, such as the amp, gpt, neo and hyg genes.

IX. *Pseudomonas* Exotoxin and Other Toxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diphtheria toxin is isolated from *Corynebacterium diphtheriae*. Ricin is the lectin RCA60 from *Ricinus communes* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD respectively (Nicholson & Blaustein, *J. Biochim. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al., *Nature* 249:627-631 (1974) and U.S. Pat. No. 3,060,165).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

In preferred embodiments of the present invention, the toxin is *Pseudomonas* exotoxin (PE). The term "*Pseudomonas* exotoxin" as used herein refers to a full-length native (naturally occurring) PE or a PE that has been modified. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO: 14) and REDL (SEQ ID NO: 15). See Siegall, et al., *J. Biol. Chem.* 264:14256 (1989). In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The native PE sequence is provided as SEQ ID NO: 1 of commonly assigned U.S. Pat. No. 5,602, 095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., *J. Biol. Chem.* 264: 14256-14261 (1989), incorporated by reference herein.

PE employed in the present invention include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE include PE40, PE38, PE37, and PE35. PE40 is a truncated derivative of PE as previously described in the art. See, Pai, et al., *Proc. Nat'l Acad. Sci. USA* 88:3358-62 (1991); and Kondo, et al., *J. Biol. Chem.* 263:9470-9475 (1988). PE35 is a 35 kD carboxyl-terminal fragment of PE composed of a met at position 280 followed by amino acids 281-364 and 381-613 of native PE. PE37, another truncated derivative of PE, is described in U.S. Pat. No. 5,821,238. PE38 is a truncated PE pro-protein composed of amino acids 253-364 and 381-613 which is activated to its cytotoxic form upon processing within a cell (see U.S. Pat. No. 5,608,039, incorporated herein by reference).

In a particularly preferred embodiment, PE38 is the toxic moiety of the immunotoxin of this invention, however, other cytotoxic fragments, such as PE35, PE37, and PE40, are contemplated and are disclosed in U.S. Pat. Nos. 5,602,095; 5,821,238; and 4,892,827, each of which is incorporated herein by reference.

X. Detectable Labels

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

XI. Conjugation of Effector Molecules to a Targeting Moiety

In a non-recombinant embodiment of the invention, effector molecules, e.g., therapeutic, diagnostic, or detection moieties, are linked to PAGE-4 targeting moieties, such as anti-PAGE-4 antibodies, using any number of means known to those of skill in the art. Both covalent and noncovalent attachment means may be used with anti-PAGE-4 antibodies or other ligands.

The procedure for attaching an effector molecule to an antibody will vary according to the chemical structure of the EM. Polypeptides typically contain variety of functional groups; e.g., carboxylic acid (COOH), free amine (—NH$_2$) or sulfhydryl (—SH) groups, which are available for reaction with a suitable functional group on an antibody to result in the binding of the effector molecule.

Alternatively, the antibody is derivatized to expose or attach additional reactive functional groups. The derivatization may involve attachment of any of a number of linker molecules such as those available from Pierce Chemical Company, Rockford Ill.

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

XII. Pharmaceutical Compositions and Administration

Peptide and protein drugs are generally administered by parenteral means. See, e.g., Banga, A., Parenteral Controlled Delivery of Therapeutic Peptides and Proteins, in *Therapeutic Peptides and Proteins*, Technomic Publishing Co., Inc., Lancaster, Pa., 1995. The peptide and protein vaccines of the invention will typically be administered parenterally. Conveniently, this may be done by i.v., s.c. or i.m. injection. Injection by s.c. and i.m. procedures is preferable not only because they may permit a longer duration of action, but also because they are exposed to dendritic cells in the skin. These dendritic cells are important antigen presenting cells. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. See, e.g., Banja, supra.

A particulate carrier based on a synthetic polymer has been shown to act as an adjuvant to enhance the immune response, in addition to providing a controlled release. Aluminum salts may also be used as adjuvants.

In preferred embodiments, the vaccines are administered in a manner to direct the immune response to a cellular response (that is, a CTL response), rather than a humoral (antibody) response. A number of means for inducing cellular responses are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins such as tripalmitoyl-S-glycerylcysteinlyseryl-serine can be used to prime tumor specific CTL when covalently attached to an appropriate peptide. See, Deres et al., Nature, 342:561-564 (1989). Further, as the induction of neutralizing antibodies can also be primed with the same molecule conjugated to a peptide which displays an appropriate epitope, the two compositions can be combined to elicit both humoral and cell-mediated responses where that is deemed desirable.

In yet another to inducing a CTL response to an immunogenic peptide, a MHC class II-restricted T-helper epitope is added to the CTL antigenic peptide to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time. See, e.g., Chesnut et al., "Design and Testing of Peptide-Based Cytotoxic T-Cell-Mediated Immunotherapeutics to Treat Infectious Diseases and Cancer," in Powell, et al., eds., *Vaccine Design, the Subunit and Adjuvant Approach*, Plenum Press, New York, 1995.

In a preferred embodiment, the peptides or protein is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference.

By "stabilizing detergent" is meant a detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40, TWEEN 20, TWEEN 60, Zwittergent 3-12, TEEPOL HB7, and SPAN 85. These detergents are usually provided in an amount of approximately 0.05 to 0.5%, preferably at about 0.2%.

By "micelle-forming agent" is meant an agent which is able to stabilize the emulsion formed with the other components such that a micelle-like structure is formed. Such agents preferably cause some irritation at the site of injection in order to recruit macrophages to enhance the cellular response. Examples of such agents include polymer surfactants described by BASF Wyandotte publications, e.g., Schmolka, J. Am. Oil. Chem. Soc. 54:110 (1977), and Hunter et al., J. Immunol. 129:1244 (1981), PLURONIC L62LF, L101, and L64, PEG1000, and TETRONIC 1501, 150R1, 701, 901, 1301, and 130R1. The chemical structures of such agents are well known in the art. Preferably, the agent is chosen to have a hydrophile-lipophile balance (HLB) of between 0 and 2, as defined by Hunter and Bennett, J. Immun. 133:3167 (1984). The agent is preferably provided in an amount between 0.5 and 10%, most preferably in an amount between 1.25 and 5%.

The oil is chosen to promote the retention of the antigen in oil-in-water emulsion, i.e., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE, tetratetracontane, glycerol, and peanut oil or other vegetable oils. The oil is preferably provided in an amount between 1 and 10%, most preferably between 2.5 and 5%. The oil should be both biodegradable and biocompatible so that the body can break down the oil over time, and so that no adverse affects, such as granulomas, are evident upon use of the oil.

In a particularly preferred embodiment, the adjuvant is a mixture of stabilizing detergents, micelle-forming agent, and oil available under the name Provax® (IDEC Pharmaceuticals, San Diego, Calif.).

In another class of embodiments, the vaccine is in the form of DNA encoding the immunogenic peptide or the PAGE-4 protein. As noted elsewhere herein, one approach to vaccination is direct vaccination with plasmid DNA. We have had good expression of PAGE-4 protein with mammalian expression plasmids. If desired, the PAGE-4 gene, or a nucleotide sequence encoding an immunogenic peptide, can be placed under the control of a strong promoter to increase expression of the molecule. Immunization by nucleic acid constructs is well known in the art and taught, for example, in U.S. Pat. No. 5,643,578, which describes methods of immunizing vertebrates by introducing DNA encoding a desired antigen to elicit a cell-mediated or a humoral response, and U.S. Pat. Nos. 5,593,972 and 5,817,637, which describe operably linking a nucleic acid sequence encoding an antigen to regulatory sequences enabling expression.

U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS, negatively charged cage-like structures of 30-40 nm in size formed spontaneously on mixing cholesterol and Quil A (saponin). Protective immunity has been generated in a variety of experimental models of infection, including toxoplasmosis and Epstein-Barr virus-induced tumors, using ISCOMS as the delivery vehicle for antigens (Mowat and Donachie, Immunol. Today 12:383-385 (1991)). Doses of antigen as low as 1 µg encapsulated in ISCOMS have been found to produce class I mediated CTL responses. Takahashi et al., Nature 344:873-875, (1990).

In another approach to using nucleic acids for immunization, the PAGE-4 protein or an immunogenic peptide thereof can also be expressed by attenuated viral hosts or vectors or bacterial vectors. Recombinant vaccinia virus, AAV, herpesvirus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides. BCG vectors are described in, for example, Stover, Nature, 351:456-460 (1991).

In a preferred embodiment, nucleic acids encoding an immunogenic peptide or the PAGE-4 protein are introduced directly into cells. For example, the nucleic acids may be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Doseages for injection are usually around 0.5 µg/kg to about 50 mg/kg, and typically are about 0.005 mg/kg to about 5 mg/kg. See, e.g., U.S. Pat. No. 5,589,466.

In addition to the vaccines of the invention, the cell growth inhibiting chimeric molecules of this invention (i.e., PE linked to an anti-PAGE-4 antibody), can be prepared in pharmaceutical compositions. They are particularly useful for parenteral administration, such as intravenous administration or administration into a body cavity or lumen of an organ. For example, metastases of prostate or testicular cancers may be treated by intravenous administration or by localized delivery to the tissue surrounding the tumor. To treat ovarian cancers, the pharmaceutical compositions of this invention can be administered directly into the pleural or peritoneal cavities.

The compositions for administration will commonly comprise a solution of the cell growth inhibiting chimeric molecules dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a pharmaceutical composition of the present invention for intravenous administration, such as an immunotoxin, would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992) both of which are incorporated herein by reference.

Polymers can be used for ion-controlled release of compositions of the present invention. Various degradable and non-degradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the compositions of the present invention, such as immunotoxins of anti-PAGE-4 antibodies and PE40, are included a variety of disease conditions caused by specific human cells that may be eliminated by the toxic action of the fusion protein. One preferred application for the immunotoxins of the invention is the treatment of malignant cells expressing PAGE-4. Exemplary malignant cells include prostate, testicular, and ovarian cancers.

XIII. Diagnostic Kits

In another embodiment, this invention provides for kits for the detection of PAGE-4-containing cells or tissues in a biological sample. A "biological sample" as used herein is a sample of biological tissue that contains PAGE-4. Such samples include, but are not limited to, tissue from biopsies, autopsies, and pathology specimens. Biological samples also include sections of tissues, such as frozen sections taken for histological purposes. A biological sample is typically obtained from a multicellular eukaryote, preferably a mammal, such as a rat, mouse, cow, dog, guinea pig, or rabbit, more preferably from a primate, such as a macaque or a chimpanzee, and most preferably from a human.

Kits for detecting the PAGE-4 protein will typically comprise an anti-PAGE-4 antibody. In some embodiments, the anti-PAGE-4 antibody will be an Fv fragment. For in vivo uses, the antibody is preferably an scFv fragment.

In addition the kits will typically include instructional materials disclosing means of use of an antibody of the present invention (e.g. for detection of PAGE-4-containing cells in a sample). The kits may also include additional components to facilitate the particular application for which the kit is designed. Thus, for example, the kit may additionally contain means of detecting a label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. Although the details of the immunoassays may vary with the particular format employed, the method of detecting PAGE-4 protein in a biological sample generally comprises the steps of contacting the biological sample with an antibody which specifically reacts, under immunologically reactive conditions, to PAGE-4. The antibody is allowed to bind under immunologically reactive conditions, and the presence of the bound antibody is detected directly or indirectly.

In an alternative set of embodiments, kits can be provided for detecting nucleic acids encoding PAGE-4 protein (a "PAGE-4 nucleic acid) in a biological sample. For example, a tissue sample from a biopsy can be tested to determine whether nucleic acids encoding PAGE-4 protein are present. Typically, the kits will provide primers which will amplify all or a portion of a PAGE-4 nucleic acid. Conveniently, the amplification is performed by polymerase chain reaction (PCR). A number of other techniques are, however, known in the art and are contemplated for use in the invention. For example, Marshall, U.S. Pat. No. 5,686,272, discloses the amplification of RNA sequences using ligase chain reaction, or "LCR." LCR has been extensively described by Landegren et al., Science, 241:1077-1080 (1988); Wu et al., Genomics, 4:560-569 (1989); Barany, in PCR Methods and Applications, 1:5-16 (1991); and Barany, Proc. Natl. Acad. Sci. USA, 88:189-193 (1991). Or, the RNA can be reverse transcribed into DNA and then amplified by LCR, PCR, or other methods. An exemplar protocol for conducting reverse transcription of RNA is taught in U.S. Pat. No. 5,705,365. Selection of appropriate primers and PCR protocols are taught, for example, in Innis, M., et al., eds., PCR Protocols 1990 (Academic Press, San Diego Calif.).

In addition the kits will typically include instructional materials disclosing means of use for the primers (e.g. for detection of PAGE-4-containing cells in a sample). The kits may also include additional components to facilitate the particular application for which the kit is designed. The kits may additionally include buffers and other reagents routinely used for the practice of a particular method. Such kits and appropriate contents are well known to those of skill in the art.

EXAMPLES

Example 1

Computer Analysis of EST Sequences

The NCBI dbEST/CGAP database (http://www.ncbi.nlm.nih.gov/ncicgap (Emmert-Buck et al., *Science* 274:998-1101 (1996); Krizman, D. B. et al., *Cancer Res.* 56:5380-5383 (1996); Strausberg, R. L. et al., *Nat. Genet.* 16:415-516 (1997)), was used as a source for cDNA sequences. The ESTs from human tissues and tumors were downloaded from ftp://ncbi.nlm.nih.gov/repository/dbEST. The cDNA libraries that we processed are listed in http://www.nci.nlm.nih.gov/UniGene/Hs.Home.html; http://www-bio.llnl.gov/bbrp/image/humlib_info.html; http://genome.wustl.edu/est/est_protocols/libraries.html; http://inhouse.ncbi.nlm.nih.gov/cgi-bin/UniGenel/browse?org=Hs&OTP=cgap. The EST sequences were clustered and sorted as described before (Vasmatzis, G. et al., *Proc. Natl. Acad. Sci., USA* 95:300-304 (1998)). However, the candidate gene list was updated by using the EST dataset of Apr. 25, 1998. This dataset contains 1,001,294 human EST sequences from 656 libraries. Two updated candidate lists were prepared, one with the specificity cutoff for prostate of three as before and another with the cutoff value of six.

Example 2

Molecular Biology Techniques

EST-plasmids were obtained from the IMAGE Consortium (Genome Systems, Inc., St. Louis, Mo.). The identities of the sequences were confirmed and extended by automated fluorescent DNA sequencing using an Applied Biosystem's Rhodamine-terminator cycle sequencing kit. PCR was performed on a Biometra Thermocycler using Boehringer Mannheim high fidelity reagent kits and the Hot-Start Technique. Northern blots containing 2 μg poly A mRNA from various tissues and cancer cell lines (CLONTECH Laboratories, Inc., Palo Alto, Calif.), blots with 20 μg/lane total tumor RNA (Invitrogen Corp., Carlsbad, Calif.), mRNA dot blots (Clontech), and a Somatic Cell Hybrid Southern Blot (Oncor, Inc., Gaithersburg, Md.) were hybridized with random primed $^{32}$P labeled DNA fragments. The specific activity of the labeled probe was 1 mCi/μg. The membranes were blocked for 4 hrs in hybridization solution (50% formamide without probe), hybridized for 15 hrs with the probe at 55° C., rinsed in 2×SSC/0.1% SDS, washed once with 2×SSC/0.1% SDS and twice with 0.2×SSC/0.1% SDS at 55° C.

Example 3

Generation of Antibodies

An exemplary PAGE-4 peptide was selected to demonstrate that the PAGE-4 protein could be used to generate antibodies. The sequence used was, in single letter code, EGTPPIEERKVEGDC (SEQ ID NO: 16).

The peptide was conjugated with keyhole limpet hemacyanin and used to immunize two New England White rabbits. Immunizations took place on days 0, 14, 28, 42, 56, and 70. For the first immunization, the peptide was emulsified with complete Freund's adjuvant and 200 μg of peptide was injected in sufficient adjuvant to make a total volume of 200 μl. For all following immunization, 100 μg of peptide was emulsified in enough incomplete Freund's adjuvant for a total injection volume of 200 μl. Serum was collected at days 49, 63, and 77, and analyzed by ELISA.

Example 4

Expression of Plasmids Encoding PAGE-4

PAGE-4 open reading frame was cloned in frame into pET 23a vector with a His tag at the 3' end. The recombinant plasmid was then transformed into *E. Coli* BL 21 (DE3) cells. Cells were grown in liquid culture and PAGE-4 expression was induced with isopropyl-B-D-thiogalactopyranoside ("IPTG"). PAGE-4 protein was purified from the cell lysate using a Ni(2+)-NTA-agarose gel column (Invitrogen).

Example 5

Immunization with DNA Encoding PAGE-4 Protein

A group of 6 male and 6 female BALB/c mice is injected intradermally with a pCR3.1 vector (Invitrogen) with a pCRPage4 plasmid. The injections comprise 15 µg of DNA in 100 µl of saline solution (0.15 molar) per injection per mouse, and are given every other week for a total of three injections. Sera is collected two weeks after the third injection and tested by ELISA on recombinant PAGE-4. If higher titer is desired, additional injections will be given. If desired, CTLs from the immunized mice can also be tested for activation against PAGE-4-expressing cells.

Although the present invention has been described in some detail by way of illustration and example for purposes of clarity of understanding, it will be obvious that certain changes and modifications may be practiced within the scope of the appended claims. All publications and patents mentioned in this specification are herein incorporated by reference into the specification to the same extent as if each individual publication or patent was specifically and individually indicated to be incorporated herein by reference.

Table 1

Comparison of the Distribution of Page-4 Sequences in EST Libraries with Page-4 Northern Hybridization Signals.

The human cDNA sequence libraries (dataset of Apr. 25, 1998) were processed by computer analyses as previously described (Vasmatzis, Proc. Natl. Acad. Sci. USA 95:300-304 (1998)). Individual PAGE-4 ESTs are nh24e10.s1, nc27g01.r1, nh24a11.s1, nf19h11.s1, nr35f13.s1 (prostate), nh32c16.s1, nt72b09.s1, nc33g02.s1/r1, nc79f08.s1/r1, nt78f11.s1, (prostate cancer), EST81031, EST80996, C18969, C18137, yi82c07.s1/r1, yw73c12.s1/r1 (placenta) and zr65g11.s1/r1, aa07e08.s1 (uterus; see note marked by asterisk (*)).

Note (*): The ESTs with uterus-specificity were part of pooled uterus-containing libraries; the other tissues of this library did not show any PAGE-4 expression in hybridization analyses. % PAGE-4/tissue: the number of PAGE-4 ESTs was divided by the total number of tissues specific ESTs. Original dot blot and Northern results are shown in FIG. 2. (+, ++, +++) indicate the signal intensity on the dot blots or Northern blots: signal, strong signal and very strong signal, respectively. Ovary gave a very weak signal after prolonged exposure of the autoradiograph.

Note (#): Other tissues in the database analysis are those that were represented by dbEST files in May 1998. Other tissues that were tested by hybridization analyses were brain, spinal cord, heart, aorta, skeletal muscle, colon, bladder, stomach, pancreas, pituitary, adrenal, thyroid, salivary, mammary, kidney, liver, small intestine, spleen, thymus, peripheral leukocyte, lymph node, bone marrow, appendix, lung, trachea, fetal brain, fetal heart, fetal kidney, fetal liver, fetal spleen, fetal thymus, fetal lung, and cancer cell lines HL60, HeLa, K562, Molt4, Raji, SW480, A549 and G361.

TABLE 1

Comparison of the distribution of PAGE-1 sequences in EST libraries with PAGE-4 Northern hybridization signals.

| | Computational Analysis | | mRNA Analysis | | |
|---|---|---|---|---|---|
| | # of PAGE-4 Tissue ESTs | % PAGE-4/ Tissue ESTs | Dot Blot | Northern | RT-PCR |
| Prostate | 5 | 5/22,334 (0.022%) | ++ | ++ | + |
| Prostate ca. | 7 | 7/20,871 (0.031%) | | | + |
| Testis | 0 | 0/31,263 | + | + | |
| Testis ca. | 0 | 0/1,123 | | | + |
| Uterus | 3* | 0/22,333 (0.013%) | + | + | |
| Uterus Ca. | | 0/1,112 | | ++ | |
| Ovary | 0 | 0/5,573 | (+) | – | |
| Ovary Ca. | 0 | 0/21,989 | | – | |
| Fallopian tube | 0 | 0/0 | ++ | | |
| Placenta | 8 | 8/49,467 (0.016%) | +++ | +++ | + |
| Other tissues/ca. # | 0* | 0/823,754 | – | – | – |

TABLE 2

Distribution of other members of PAGE-4-like ESTs in the database. ESTs with homology to PAGE-4 were identified by BLAST and FASTA (Altschul, S., et at., J. Mol. Biol., 215:403-410 (1990); Pearson, W, et at., Proc. Natl. Acad. Sci. USA, 85:2444-2448 (1988). "/Ca." indicates ESTs from tumor libraries. PAGE 2 and PAGE 3 are sequences that are more homologous to PAGE than to any member of the GAGE protein family (see FIGS. 1 and 2).

| | Tissue Distribution | | | | | |
|---|---|---|---|---|---|---|
| EST Cluster | Prostate/Ca, | Testis | Placenta | Germ Cell/Ca. | Pool (w/Uterus) | Pool (w/Testis) |
| PAGE 1 | nh24e10 | | yw73c12 | | | aa07e08 |
| | nc24a11 | | y182c07 | | | zr65g11 |
| | nh27g01 | | C18137 | | | |
| | nf19h11 | | C18969 | | | |
| | nr35f03 | | EST80996 | | | |
| | nh32c06/Ca. | | EST81031 | | | |
| | nc33g02/Ca. | | | | | |
| | nt72b09/Ca. | | | | | |
| | nt78f01/Ca. | | | | | |
| | nc79f08/Ca. | | | | | |

TABLE 2-continued

Distribution of other members of PAGE-4-like ESTs in the database. ESTs with homology to PAGE-4 were identified by BLAST and FASTA (Altschul, S., et at., J. Mol. Biol., 215:403-410 (1990); Pearson, W, et at., Proc. Natl. Acad. Sci. USA, 85:2444-2448 (1988). "/Ca." indicates ESTs from tumor libraries. PAGE 2 and PAGE 3 are sequences that are more homologous to PAGE than to any member of the GAGE protein family (see FIGS. 1 and 2).

| EST Cluster | Prostate/Ca, | Testis | Placenta | Germ Cell/Ca. | Pool (w/Uterus) | Pool (w/Testis) |
|---|---|---|---|---|---|---|
| PAGE 2 | | ai61a04 | | om69f10/Ca. | | om13c03 |
| | | zv62h08 | | | | oj89d1 |
| | | aj29d06 | | | | |
| | | zv58h12 | | | | |
| PAGE 3 | | | | | | om29f08 |

What is claimed is:

1. An isolated polypeptide comprising:
   (a) an amino acid sequence set forth as SEQ ID NO: 1; or
   (b) 8 to 11 contiguous amino acids of SEQ ID NO: 1, wherein the polypeptide binds major histocompatibility complex (MHC) I.

2. The isolated polypeptide of claim 1, comprising an amino acid sequence set forth as SEQ ID NO: 1.

3. An isolated polypeptide consisting of 8 to 11 contiguous amino acids of SEQ ID NO: 1, wherein the polypeptide binds major histocompatibility complex (MHC) I.

4. The isolated polypeptide of claim 3, wherein the polypeptide is 9 to 10 amino acids in length.

5. The isolated polypeptide of claim 2, wherein the polypeptide binds HLA-A1, HLA-A2.1, HLA-A3.2, HLA-A4.1 or HLA-A 11.2.

6. The isolated polypeptide of claim 3, conjugated to a lipid.

7. An immunogenic composition comprising the isolated polypeptide of claim 2, and a pharmaceutically acceptable carrier.

8. An immunogenic composition comprising the isolated polypeptide of claim 3, and a pharmaceutically acceptable carrier.

9. The isolated polypeptide of claim 3, wherein the isolated polypeptide is conjugated to a lipid.

10. The immunogenic composition of claim 7, further comprising two or more of a stabilizing detergent, a micelle-forming agent, and an oil.

11. The immunogenic composition of claim 8, further comprising two or more of a stabilizing detergent, a micelle-forming agent, and an oil.

* * * * *

SEQUENCE LISTING

<160> NUMBER OF SEQ ID NOS: 16

<210> SEQ ID NO 1
<211> LENGTH: 102
<212> TYPE: PRT
<213> ORGANISM: Homo sapiens

<400> SEQUENCE: 1

```
Met Ser Ala Arg Val Arg Ser Arg Ser Arg Gly Arg Gly Asp Gly Gln
1               5                   10                  15

Glu Ala Pro Asp Val Val Ala Phe Val Ala Pro Gly Glu Ser Gln Gln
            20                  25                  30

Glu Glu Pro Pro Thr Asp Asn Gln Asp Ile Glu Pro Gly Gln Glu Arg
        35                  40                  45

Glu Gly Thr Pro Pro Ile Glu Glu Arg Lys Val Glu Gly Asp Cys Gln
    50                  55                  60

Glu Met Asp Leu Glu Lys Thr Arg Ser Glu Arg Gly Asp Gly Ser Asp
65                  70                  75                  80

Val Lys Glu Lys Thr Pro Pro Asn Pro Lys His Ala Lys Thr Lys Glu
                85                  90                  95

Ala Gly Asp Gly Gln Pro
            100
```

<210> SEQ ID NO 2
<211> LENGTH: 117
<212> TYPE: PRT
<213> ORGANISM: Homo sapiens

<400> SEQUENCE: 2

```
Met Ser Trp Arg Gly Arg Ser Thr Tyr Arg Pro Arg Pro Arg Arg Tyr
1               5                   10                  15

Val Glu Pro Pro Glu Met Ile Gly Pro Met Arg Pro Glu Gln Phe Ser
            20                  25                  30

Asp Glu Val Glu Pro Ala Thr Pro Glu Glu Gly Glu Pro Ala Thr Gln
        35                  40                  45

Arg Gln Asp Pro Ala Ala Ala Gln Glu Gly Glu Asp Glu Gly Ala Ser
    50                  55                  60

Ala Gly Gln Gly Pro Lys Pro Glu Ala Asp Ser Gln Glu Gln Gly His
65                  70                  75                  80
```

```
Pro Gln Thr Gly Cys Glu Cys Glu Asp Gly Pro Asp Gly Gln Glu Met
            85                  90                  95

Asp Pro Pro Asn Pro Glu Val Lys Thr Pro Glu Glu Met Arg
            100                 105                 110

Ser His Tyr Val Ala
        115

<210> SEQ ID NO 3
<211> LENGTH: 116
<212> TYPE: PRT
<213> ORGANISM: Homo sapiens

<400> SEQUENCE: 3

Met Ser Trp Arg Gly Arg Ser Thr Tyr Arg Pro Arg Pro Arg Tyr
1               5                   10                  15

Val Glu Pro Pro Glu Met Ile Gly Pro Met Arg Pro Glu Gln Phe Ser
            20                  25                  30

Asp Val Glu Pro Ala Thr Pro Glu Glu Gly Glu Pro Ala Thr Gln
            35                  40                  45

Arg Gln Asp Pro Ala Ala Gln Glu Gly Glu Asp Glu Gly Ala Ser
        50                  55                  60

Ala Gly Gln Gly Pro Lys Pro Glu Ala His Ser Gln Glu Gln Gly His
65                  70                  75                  80

Pro Gln Thr Gly Cys Glu Cys Glu Asp Gly Pro Asp Gly Gln Glu Met
            85                  90                  95

Asp Pro Pro Asn Pro Glu Val Lys Thr Pro Glu Glu Gly Glu Lys
            100                 105                 110

Gln Ser Gln Cys
        115

<210> SEQ ID NO 4
<211> LENGTH: 118
<212> TYPE: PRT
<213> ORGANISM: Homo sapiens

<400> SEQUENCE: 4

Met Asn Leu Ser Arg Gly Lys Ser Thr Tyr Tyr Arg Pro Arg Pro Arg
1               5                   10                  15

Arg Tyr Val Gln Pro Pro Glu Val Ile Gly Pro Met Arg Pro Glu Gln
            20                  25                  30

Phe Ser Asp Glu Val Glu Pro Ala Thr Pro Glu Glu Gly Glu Pro Ala
            35                  40                  45

Thr Gln Arg Gln Asp Pro Ala Ala Gln Glu Gly Glu Asp Glu Gly
        50                  55                  60

Ala Ser Ala Gly Gln Gly Pro Lys Pro Glu Ala Asp Ser Gln Glu Gln
65                  70                  75                  80

Gly His Pro Gln Thr Gly Cys Glu Cys Glu Asp Gly Pro Asp Gly Gln
            85                  90                  95

Glu Met Asp Pro Pro Asn Pro Glu Val Lys Thr Pro Glu Glu Gly
            100                 105                 110

Glu Lys Gln Ser Gln Cys
        115

<210> SEQ ID NO 5
<211> LENGTH: 117
<212> TYPE: PRT
<213> ORGANISM: Homo sapiens
```

<400> SEQUENCE: 5

```
Met Ser Trp Arg Gly Arg Ser Thr Tyr Tyr Arg Pro Arg Pro Arg Arg
1               5                   10                  15

Tyr Val Gln Pro Pro Glu Met Ile Gly Pro Met Arg Pro Glu Gln Phe
            20                  25                  30

Ser Asp Glu Val Glu Pro Ala Thr Pro Glu Glu Gly Glu Pro Ala Thr
        35                  40                  45

Gln Arg Gln Asp Pro Ala Ala Ala Gln Glu Gly Glu Asp Glu Gly Ala
    50                  55                  60

Ser Ala Gly Gln Gly Pro Lys Pro Glu Ala Asp Ser Gln Glu Gln Gly
65                  70                  75                  80

His Pro Gln Thr Gly Cys Glu Cys Glu Asp Gly Pro Asp Gly Gln Glu
                85                  90                  95

Met Asp Pro Pro Asn Pro Glu Glu Val Lys Thr Pro Glu Glu Gly Glu
            100                 105                 110

Lys Gln Ser Gln Cys
        115
```

<210> SEQ ID NO 6
<211> LENGTH: 117
<212> TYPE: PRT
<213> ORGANISM: Homo sapiens

<400> SEQUENCE: 6

```
Met Ser Trp Arg Gly Arg Ser Thr Tyr Tyr Arg Pro Arg Pro Arg Arg
1               5                   10                  15

Tyr Val Gln Pro Pro Glu Val Ile Gly Pro Met Arg Pro Glu Gln Phe
            20                  25                  30

Ser Asp Glu Val Glu Pro Ala Thr Pro Glu Glu Gly Glu Pro Ala Thr
        35                  40                  45

Gln Arg Gln Asp Pro Ala Ala Ala Gln Glu Gly Glu Asp Glu Gly Ala
    50                  55                  60

Ser Ala Gly Gln Gly Pro Lys Pro Glu Ala Asp Ser Gln Glu Gln Gly
65                  70                  75                  80

His Pro Gln Thr Gly Cys Glu Cys Glu Asp Gly Pro Asp Gly Gln Glu
                85                  90                  95

Met Asp Pro Pro Asn Pro Glu Glu Val Lys Thr Pro Glu Glu Gly Glu
            100                 105                 110

Lys Gln Ser Gln Cys
        115
```

<210> SEQ ID NO 7
<211> LENGTH: 117
<212> TYPE: PRT
<213> ORGANISM: Homo sapiens

<400> SEQUENCE: 7

```
Met Ser Trp Arg Gly Arg Ser Thr Tyr Tyr Arg Pro Arg Pro Arg Arg
1               5                   10                  15

Tyr Val Gln Pro Pro Glu Val Ile Gly Pro Met Arg Pro Glu Gln Phe
            20                  25                  30

Ser Asp Glu Val Glu Pro Ala Thr Pro Glu Glu Gly Glu Pro Ala Thr
        35                  40                  45

Gln Arg Gln Asp Pro Ala Ala Ala Gln Glu Gly Glu Asp Glu Gly Ala
    50                  55                  60

Ser Ala Gly Gln Gly Pro Lys Pro Glu Ala Asp Ser Gln Glu Gln Gly
```

-continued

```
                65                  70                  75                  80
        His Pro Gln Thr Gly Cys Glu Cys Glu Asp Gly Pro Asp Gly Gln Glu
                            85                  90                  95
        Val Asp Pro Asn Pro Glu Glu Val Lys Thr Pro Glu Glu Gly Glu
                        100                 105                 110
        Lys Gln Ser Gln Cys
                115
```

<210> SEQ ID NO 8
<211> LENGTH: 124
<212> TYPE: PRT
<213> ORGANISM: Homo sapiens

<400> SEQUENCE: 8

```
Met Ser Leu Glu Gln Lys Ser Gln His Cys Lys Pro Glu Glu Gly Leu
1               5                   10                  15
Asp Thr Gln Glu Glu Ala Leu Gly Leu Val Gly Val Gln Ala Ala Thr
                20                  25                  30
Thr Glu Glu Gln Glu Ala Val Ser Ser Ser Pro Leu Val Pro Gly
            35                  40                  45
Thr Leu Gly Glu Val Pro Ala Ala Gly Ser Pro Gly Pro Leu Lys Ser
        50                  55                  60
Pro Gln Gly Ala Ser Ala Ile Pro Thr Ala Ile Asp Phe Thr Leu Trp
65                  70                  75                  80
Arg Gln Ser Ile Lys Gly Ser Ser Asn Gln Glu Glu Glu Gly Pro Ser
                85                  90                  95
Thr Ser Pro Asp Pro Glu Ser Val Phe Arg Ala Ala Leu Ser Lys Lys
                100                 105                 110
Val Ala Asp Leu Ile His Phe Leu Leu Leu Lys Tyr
                115                 120
```

<210> SEQ ID NO 9
<211> LENGTH: 127
<212> TYPE: PRT
<213> ORGANISM: Homo sapiens

<400> SEQUENCE: 9

```
Met Leu Leu Gly Gln Lys Ser Gln Arg Tyr Lys Ala Glu Glu Gly Leu
1               5                   10                  15
Gln Ala Gln Gly Glu Ala Pro Gly Leu Met Asp Val Gln Ile Pro Thr
                20                  25                  30
Ala Glu Glu Gln Lys Ala Ala Ser Ser Ser Thr Leu Ile Met Gly
            35                  40                  45
Thr Leu Glu Glu Val Thr Asp Ser Gly Ser Pro Ser Pro Gln Ser
        50                  55                  60
Pro Glu Gly Ala Ser Ser Ser Leu Thr Val Thr Asp Ser Thr Leu Trp
65                  70                  75                  80
Ser Gln Ser Asp Glu Gly Ser Ser Asn Glu Glu Glu Gly Pro Ser
                85                  90                  95
Thr Ser Pro Asp Pro Ala His Leu Glu Ser Leu Phe Arg Glu Ala Leu
                100                 105                 110
Asp Glu Lys Val Ala Glu Leu Val Arg Phe Leu Leu Arg Lys Tyr
                115                 120                 125
```

<210> SEQ ID NO 10
<211> LENGTH: 87
<212> TYPE: PRT

```
<213> ORGANISM: Artificial Sequence
<220> FEATURE:
<223> OTHER INFORMATION: PAGE1

<400> SEQUENCE: 10

Met Ser Ala Arg Val Arg Ser Arg Ser Arg Gly Arg Gly Asp Gly Gln
1               5                   10                  15

Glu Ala Pro Asp Val Val Ala Phe Val Ala Pro Gly Glu Ser Gln Glu
                20                  25                  30

Glu Glu Pro Pro Thr Asp Asn Gln Gly Pro Asp Met Glu Ala Phe Gln
            35                  40                  45

Gln Glu Leu Asp Leu Glu Lys Thr Arg Ser Glu Arg Gly Asp Gly Ser
        50                  55                  60

Asp Val Lys Glu Lys Thr Pro Pro Asn Pro Lys His Ala Lys Thr Lys
65                  70                  75                  80

Glu Ala Gly Asp Gly Gln Pro
                85

<210> SEQ ID NO 11
<211> LENGTH: 109
<212> TYPE: PRT
<213> ORGANISM: Artificial Sequence
<220> FEATURE:
<223> OTHER INFORMATION: PAGE2

<400> SEQUENCE: 11

Met Ser Glu Leu Val Arg Ala Arg Ser Gln Ser Ser Glu Arg Gly Asn
1               5                   10                  15

Asp Gln Glu Ser Ser Gln Pro Val Gly Ser Val Ile Val Gln Glu Pro
                20                  25                  30

Thr Glu Glu Lys Arg Gln Gln Glu Glu Pro Pro Thr Asp Asn Gln Asp
            35                  40                  45

Ile Glu Pro Gly Gln Glu Arg Glu Gly Thr Pro Ile Glu Glu Arg
        50                  55                  60

Lys Val Glu Gly Asp Cys Gln Glu Met Ala Leu Leu Lys Ile Glu Asp
65                  70                  75                  80

Glu Pro Gly Asp Gly Pro Asp Val Arg Glu Gly Ile Met Pro Thr Phe
                85                  90                  95

Asp Leu Thr Lys Val Leu Glu Ala Gly Asp Ala Gln Pro
            100                 105

<210> SEQ ID NO 12
<211> LENGTH: 79
<212> TYPE: PRT
<213> ORGANISM: Homo sapiens

<400> SEQUENCE: 12

Met Thr Ser Phe Asn Lys Thr Ala Pro Pro Ile Glu Ser Gln Asp Tyr
1               5                   10                  15

Thr Pro Gly Gln Glu Arg Asp Glu Gly Ala Leu Asp Phe Gln Val Pro
                20                  25                  30

Ser Leu Ala Ala Tyr Leu Trp Glu Leu Thr Arg Pro Lys Thr Gly Gly
            35                  40                  45

Glu Arg Gly Asp Gly Pro Asn Val Lys Gly Glu Ser Leu Pro Asn Leu
        50                  55                  60

Glu Pro Val Lys Ile Pro Glu Ala Gly Glu Gly Gln Pro Ser Val
65                  70                  75
```

```
<210> SEQ ID NO 13
<211> LENGTH: 476
<212> TYPE: DNA
<213> ORGANISM: Homo sapiens

<400> SEQUENCE: 13
gaagaattcg ccaggctctc tgctgactca agttcttcag ttcacgatct tctagttgca      60
gcgatgagtg cacgagtgag atcaagatcc agaggaagag gagatggtca ggaggctccc     120
gatgtggttg cattcgtggc tcccggtgaa tctcagcaag aggaaccacc aactgacaat     180
caggatattg aacctggaca agagagagaa ggaacacctc cgatcgaaga acgtaaagta     240
gaaggtgatt gccaggaaat ggatctggaa aagactcgga gtgagcgtgg agatggctct     300
gatgtaaaag agaagactcc acctaatcct aagcatgcta agactaaaga agcaggagat     360
gggcagccat aagttaaaaa aagacaagc tgaagctaca cacatggctg atgtcacatt     420
gaaaatgtga ctgaaaattt gaaaattctc tcaataaagt ttgagttttc tctgaa        476

<210> SEQ ID NO 14
<211> LENGTH: 4
<212> TYPE: PRT
<213> ORGANISM: Artificial Sequence
<220> FEATURE:
<223> OTHER INFORMATION: Carboxyl terminus

<400> SEQUENCE: 14

Lys Asp Glu Leu
1

<210> SEQ ID NO 15
<211> LENGTH: 4
<212> TYPE: PRT
<213> ORGANISM: Artificial Sequence
<220> FEATURE:
<223> OTHER INFORMATION: Carboxyl terminus

<400> SEQUENCE: 15

Arg Glu Asp Leu
1

<210> SEQ ID NO 16
<211> LENGTH: 15
<212> TYPE: PRT
<213> ORGANISM: Artificial Sequence
<220> FEATURE:
<223> OTHER INFORMATION: PAGE-4 peptide used to generate antibodies

<400> SEQUENCE: 16

Glu Gly Thr Pro Pro Ile Glu Glu Arg Lys Val Glu Gly Asp Cys
1               5                   10                  15
```